US012036102B2

(12) United States Patent
Lucia et al.

(10) Patent No.: US 12,036,102 B2
(45) Date of Patent: Jul. 16, 2024

(54) PACKAGING PLANT FOR GROUPS OF HYGIENIC ABSORBENT ARTICLES, TRANSPORT APPARATUS AND RELATED METHODS

(71) Applicant: Fameccanica.Data S.p.A., San Giovanni Teatino (IT)

(72) Inventors: Oronzo Lucia, Pescara (IT); Massimiliano Rossetti, Pescara (IT); Francesco D'Aponte, Pescara (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 0 days.

(21) Appl. No.: 17/760,509

(22) PCT Filed: Sep. 8, 2020

(86) PCT No.: PCT/IB2020/058329
§ 371 (c)(1),
(2) Date: Mar. 15, 2022

(87) PCT Pub. No.: WO2021/053456
PCT Pub. Date: Mar. 25, 2021

(65) Prior Publication Data
US 2023/0255834 A1    Aug. 17, 2023

(30) Foreign Application Priority Data

Sep. 17, 2019 (IT) .......................... 102019000016412
Sep. 17, 2019 (IT) .......................... 102019000016415
Sep. 17, 2019 (IT) .......................... 102019000016421

(51) Int. Cl.
*B65B 35/46*    (2006.01)
*A61F 13/15*    (2006.01)
(Continued)

(52) U.S. Cl.
CPC .. *A61F 13/15764* (2013.01); *A61F 13/15747* (2013.01); *A61F 13/15772* (2013.01);
(Continued)

(58) Field of Classification Search
CPC .......... A61F 13/15747; A61F 13/15772; A61F 13/15804; A61F 13/551; B65B 35/54;
(Continued)

(56) References Cited

U.S. PATENT DOCUMENTS 6,721,627 B2 *  4/2004  Udou ................... B65G 1/0485
                                                  198/465.1
7,478,749 B2 *  1/2009  Clothier ............... G06Q 10/087
                                                  235/383
(Continued)

FOREIGN PATENT DOCUMENTS

DE      4244351 A1    7/1993
DE    102017127329    8/2020
(Continued)

OTHER PUBLICATIONS

Written Opinion of the International Preliminary Examining Authority dated Feb. 15, 2021 (9 pages).
(Continued)

*Primary Examiner* — Douglas A Hess
(74) *Attorney, Agent, or Firm* — RMCK Law Group PLC

(57) ABSTRACT

A packaging plant of groups of absorbent sanitary articles able to create various types of customized packages in relation to the needs of consumers, automatically and without interruptions in the production of absorbent sanitary articles. The present invention also relates to a method for managing a packaging plant. The present invention also relates to a transport apparatus for absorbent sanitary articles, as well as to a method for transporting absorbent sanitary articles.

12 Claims, 5 Drawing Sheets

Figure 6:
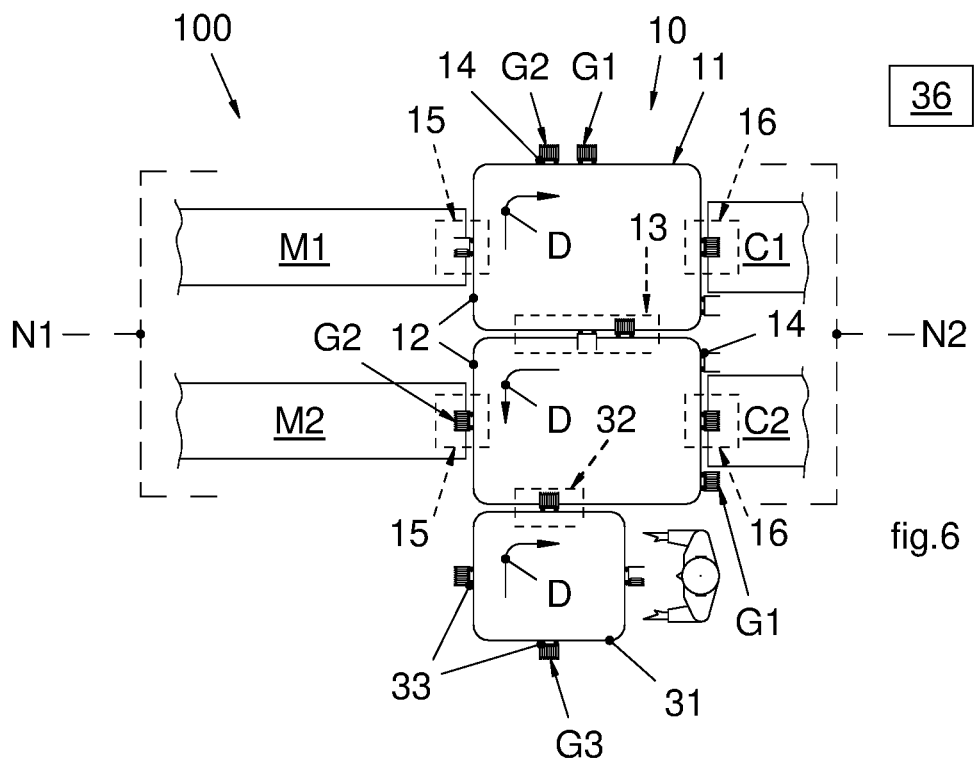

(51) Int. Cl.
*A61F 13/551* (2006.01)
*B65B 35/54* (2006.01)
*B65B 65/00* (2006.01)
*B65G 37/02* (2006.01)
*B65G 54/02* (2006.01)

(52) U.S. Cl.
CPC ...... *A61F 13/15804* (2013.01); *A61F 13/551* (2013.01); *B65B 35/46* (2013.01); *B65B 65/006* (2013.01); *B65G 37/02* (2013.01); *B65G 54/02* (2013.01)

(58) Field of Classification Search
CPC ....... B65B 35/46; B65B 65/006; B65G 37/02; B65G 54/02; G01N 35/04; G01N 2035/0477
See application file for complete search history.

(56) References Cited

U.S. PATENT DOCUMENTS

| | | | | |
|---|---|---|---|---|
| 8,096,409 B2* | 1/2012 | Wipf | ...................... | B65G 19/02 |
| | | | | 198/805 |
| 8,776,985 B2* | 7/2014 | Huettner | ................ | B65G 54/02 |
| | | | | 198/459.8 |
| 9,315,334 B2* | 4/2016 | Mellars | .................. | B65G 43/00 |
| 9,327,855 B2* | 5/2016 | Hurni | ..................... | B65G 54/02 |
| 9,889,954 B2* | 2/2018 | Gasber | .................. | B65B 25/008 |
| 10,106,331 B2* | 10/2018 | Radak | .................... | B65G 43/00 |
| 10,167,143 B2* | 1/2019 | Senn | ........................ | B65G 37/02 |
| 10,737,403 B2* | 8/2020 | Bauer | ...................... | B26D 7/32 |
| 11,698,626 B2* | 7/2023 | Burkhard | ............... | G06Q 50/04 |
| | | | | 700/115 |
| 11,912,454 B2* | 2/2024 | D'Aponte | ............... | B65B 57/00 |
| 2003/0149509 A1 | 8/2003 | Udou et al. | | |
| 2018/0074478 A1 | 3/2018 | Burkhard et al. | | |
| 2018/0265230 A1 | 9/2018 | Burk et al. | | |

FOREIGN PATENT DOCUMENTS

| | | |
|---|---|---|
| EP | 3183972 A1 | 6/2017 |
| EP | 3214024 A1 | 9/2017 |
| EP | 3422562 A1 | 1/2019 |
| JP | H01271312 A | 10/1989 |
| WO | 2015162182 A1 | 10/2015 |
| WO | 2016071062 A1 | 5/2016 |
| WO | 2018167436 A1 | 9/2018 |
| WO | 2018210529 A1 | 11/2018 |

OTHER PUBLICATIONS

International Preliminary Report on Patentability dated Dec. 7, 2021 (9 pages).
International Search Report dated Dec. 14, 2020 and Written Opinion of the ISA (15 pages total).

* cited by examiner

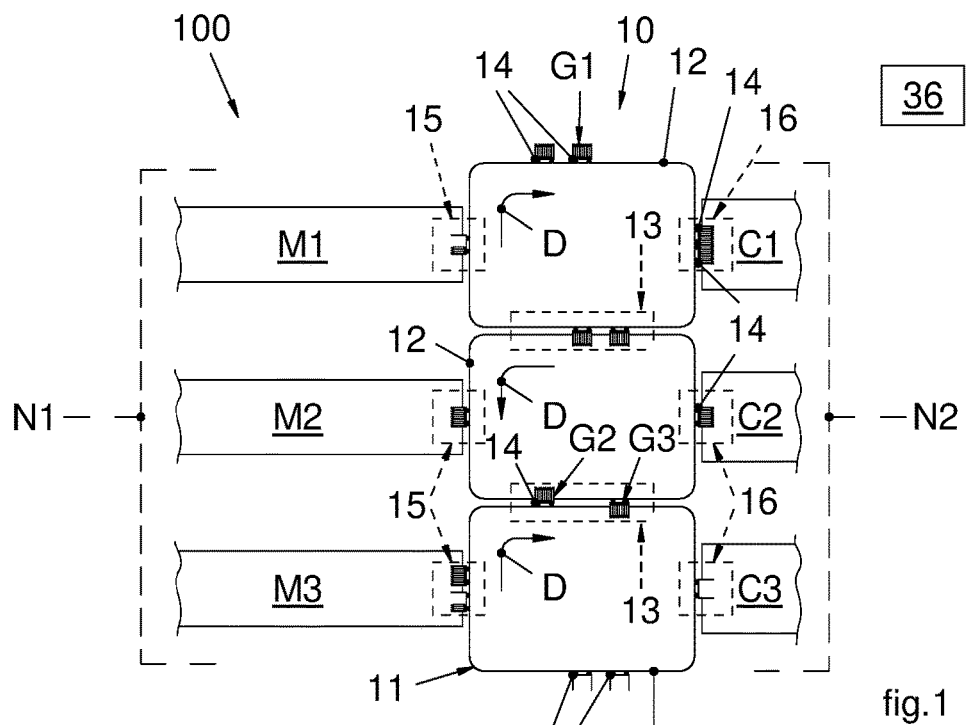
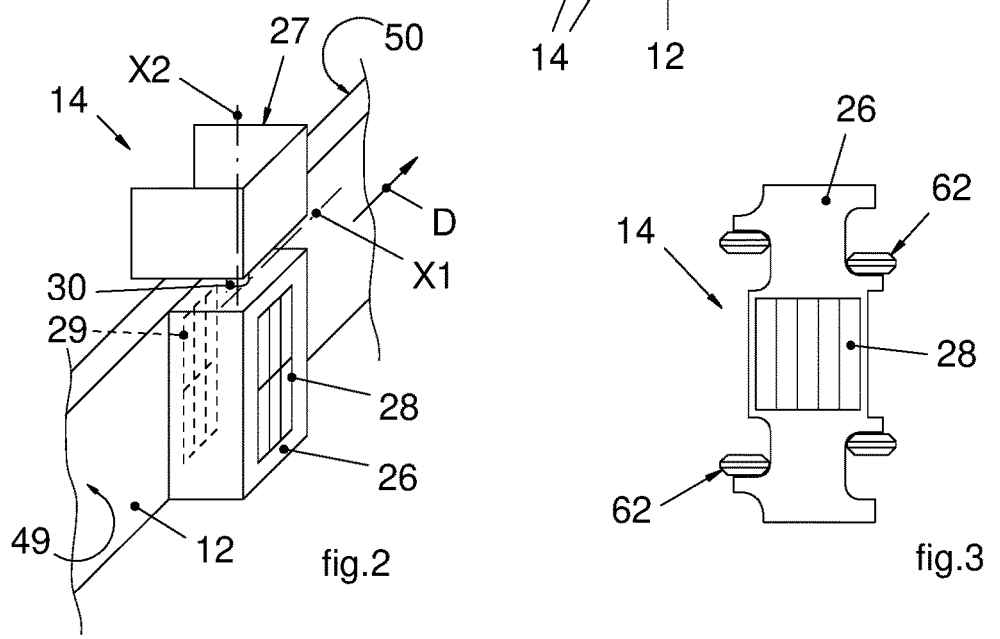
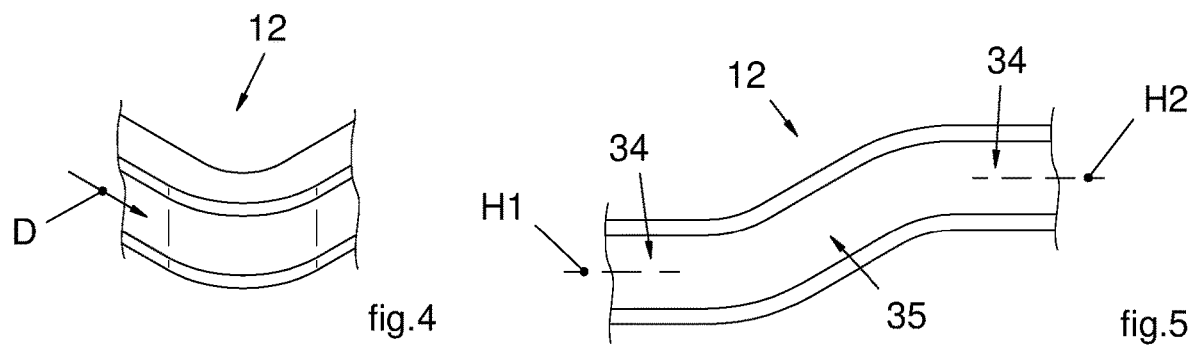

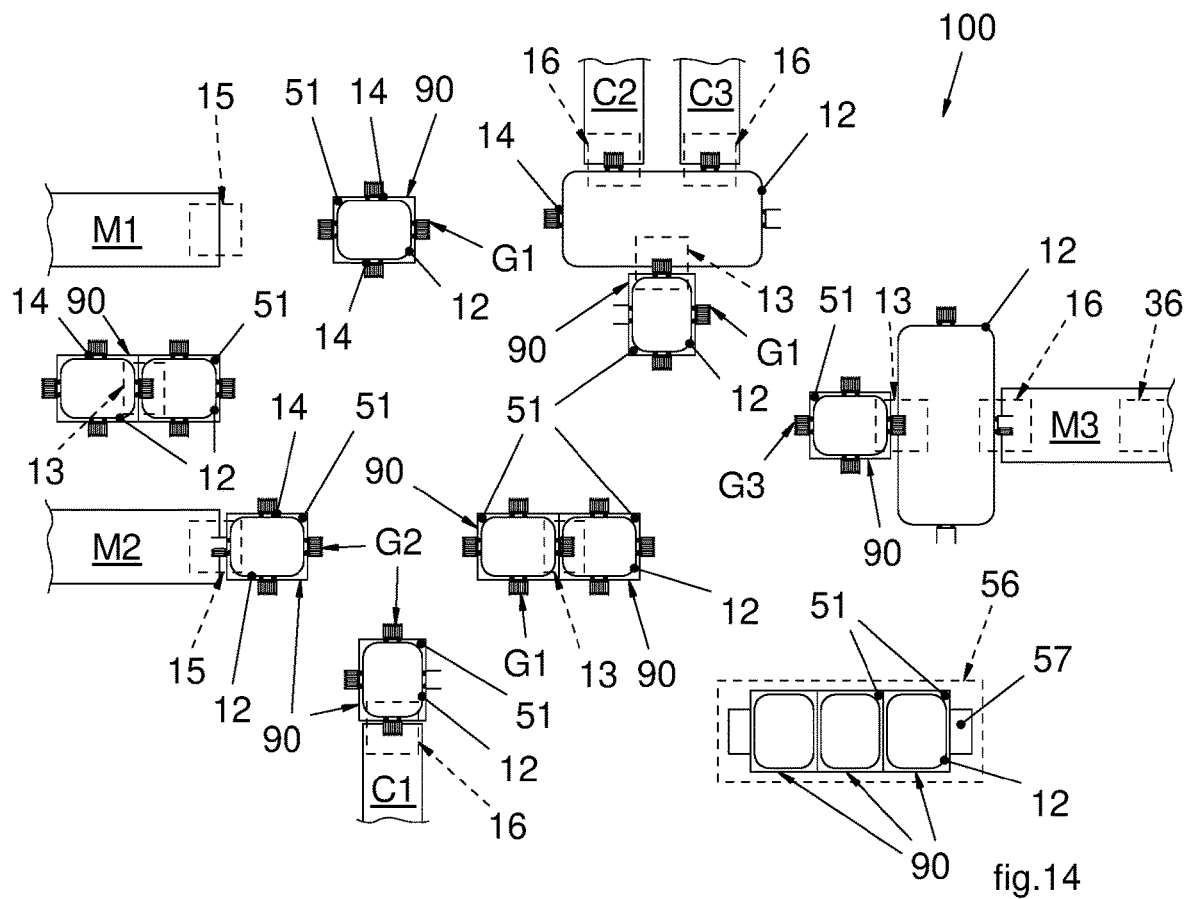
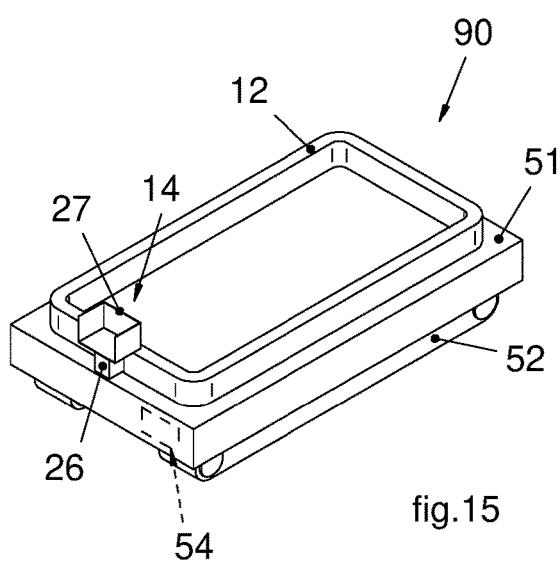
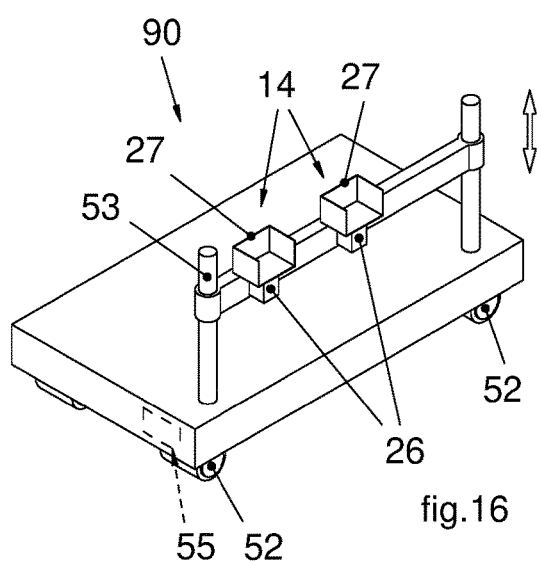

PACKAGING PLANT FOR GROUPS OF HYGIENIC ABSORBENT ARTICLES, TRANSPORT APPARATUS AND RELATED METHODS

CROSS-REFERENCE TO RELATED APPLICATIONS

This application is a 371 National Stage of International Application No. PCT/IB2020/058329, filed Sep. 8, 2020, which claims priority to Italian Patent Application No. 102019000016412 filed Sep. 17, 2019, to Italian Patent Application No. 102019000016415 filed Sep. 17, 2019, and to Italian Patent Application No. 102019000016415 filed Sep. 17, 2019. The disclosure of each of the above applications is incorporated herein by reference in its entirety.

Embodiments of the present invention relate to a plant for packaging groups of absorbent sanitary articles, such as, for example, diapers, diaper-pants, diapers for incontinence, sanitary towels, or other articles intended to absorb body fluids.

Embodiments of the present invention also relate to a method for managing a packaging plant of groups of absorbent sanitary articles.

Further embodiments also relate to a transport apparatus of absorbent sanitary articles, such as, for example, diapers, diaper-pants, diapers for incontinence, sanitary towels, or other articles intended to absorb body fluids.

Embodiments also relate to a method for transporting absorbent sanitary articles.

STATE OF THE ART

In the sector of absorbent sanitary articles, the need to create packages with a desired number and/or type of groups of absorbent sanitary articles is known. There is a need to create a plurality of packages having a number of absorbent sanitary articles that are also very different from each other.

These packages are made by packaging machines functionally connected to respective production machines that supply groups of absorbent sanitary articles, each with its own production rate.

Some packaging machines can manage and package a predefined number of absorbent sanitary articles in relation to the specific production rate of the production machine to which they are functionally connected.

By virtue of the market needs and the variety of absorbent sanitary articles available, these groups may comprise an equal or different number of articles and, moreover, they may comprise identical or different absorbent sanitary articles.

For example, a first group of absorbent sanitary articles may comprise two incontinence pads, five diapers, and thirteen female sanitary towels, and a second group of absorbent sanitary articles may comprise twenty diapers.

Those skilled in the sector are unable to meet the needs of consumers on a large scale, as efficient methods and apparatuses are not known for producing customized packages comprising groups of absorbent sanitary articles that differ every time according to the demands of the various consumers.

The solutions known in the field have not yet made it possible to process and package a plurality of combinations of groups of absorbent sanitary articles quickly.

Some known solutions envisage the packaging of a fixed number of groups of absorbent sanitary articles of the same type.

This makes it possible to only partially satisfy the demands of consumers who do not find customized packages with various groups of absorbent sanitary articles on the market.

One of the main problems encountered in known plants is that they comprise different production machines, which may have very different production rates.

This did not allow provision of an efficient solution that is able to coordinate the production of articles at different rates of packaging.

If it is necessary to package groups of absorbent sanitary articles with different numbers and/or different types of absorbent sanitary articles supplied by different production machines, it is known that these activities are carried out offline, i.e. in a grouping station not connected to the production machines. and to the packaging machines, by operators who manually group the absorbent sanitary articles in relation to the specific customized package to be created.

It is known that these solutions which involve the use of operators for manual packaging are slow and, moreover, are subject to multiple non-monitorable errors for which it is not possible to implement actions to prevent them from happening again.

Other known solutions require frequent modifications to the plant in order to process and package different combinations of groups of absorbent sanitary articles. This significantly increases costs and production times.

If it is intended to make a package comprising various groups of absorbent sanitary articles and an additional article, be it a specific absorbent sanitary article, an advertising leaflet, or another promotional article, the operators must supply these additional articles manually and supply them to the packaging machine, after interrupting the formation of the groups of absorbent sanitary articles coming from the production machines.

This leads to long and costly production stops to the detriment of the manufacturers of absorbent sanitary articles.

Other solutions envisage producing a plurality of absorbent sanitary articles and storing them in such a way as to be able to package them manually at subsequent times in relation to the customized packages requested by consumers.

These known solutions present considerable problems both from a storage point of view and from the point of view of maintaining the performance of the absorbent sanitary articles, since it is known that these absorbent sanitary articles may also remain in storage for a long time.

This entails high costs and considerable losses as the articles, deteriorating over time, can no longer be put on the market.

Other known solutions such as the one described in document US-A-2018/074478 (US'478) are scarcely flexible, since they have a plurality of processing stations connected by means of a rigid transfer apparatus and with a stable and fixed configuration that cannot be easily modified in relation to specific production needs.

In fact, the different parts of the circuit that make up the transfer apparatus described in document US'478 are physically connected to each other and, therefore, if one wishes to modify the configuration and/or the path of the transfer apparatus circuit, it would be necessary to physically disassemble the various components and replace them with others having the desired configuration. It is clear that this involves the use of a large number of operators with consequent interruption of production for prolonged and unacceptable times for the sector.

Assuming that there is only one production machine, it is known that to change the predefined number of absorbent sanitary articles that are managed and packaged by the packaging machine functionally connected thereto, it is necessary to interrupt production and intervene both on the packaging machine and on the production machine.

For example, it may be necessary to change settings, add and/or remove components, or perform other operations so that production times are adequate to allow the grouping of articles and their packaging while maintaining production continuity.

These interventions can be long, require the use of multiple operators, and also involve high costs, as well as a significant slowdown in production.

Some known solutions envisage setting the production machine so that it supplies the absorbent sanitary articles at a rate lower than the maximum rate at which the production machine itself is able to operate.

This makes it possible to manage and package groups of absorbent sanitary articles having numbers of absorbent sanitary articles that only differ by a few units.

In the latter case, once a first group of absorbent sanitary articles has been grouped, this group is moved from the grouping area to the packaging area in less time than the time necessary for the next absorbent sanitary article produced by the production machine to position itself in the grouping area that will form a second group of absorbent sanitary articles.

However, these solutions do not allow management of groups of absorbent sanitary articles having numbers of absorbent sanitary articles which differ by many units.

For example, these known solutions are unable to manage a first group consisting of ten absorbent sanitary articles and a second group consisting of three absorbent sanitary articles.

These known solutions present the additional problem that they do not allow the production of absorbent sanitary articles at the maximum rate allowed by the production machine.

This does not allow the available resources to be used efficiently and, moreover, it significantly reduces the total number of absorbent sanitary articles that can be produced in the same time.

Other known solutions envisage the use of two or more grouping areas wherein two or more groups of absorbent sanitary articles are grouped alternately.

In the latter case, while a grouping area is freed from the group of absorbent sanitary articles formed, the production machine supplies the absorbent sanitary articles in another grouping area.

In addition to requiring the use of multiple grouping systems and a selector system to supply the produced absorbent sanitary articles to the desired grouping area, these known solutions may process groups of absorbent sanitary articles having a predefined number of absorbent sanitary articles.

In this case as well, if it is intended to change the number of absorbent sanitary articles, it is necessary to intervene both on the production machine and on the packaging machine in order to appropriately synchronize the timing of the various methods including the production, grouping, packaging and transfer.

Another problem of known solutions is that it is not possible to package absorbent sanitary articles from the same production machine using different packaging machines.

For example, packaging machines capable of grouping absorbent sanitary articles with a desired orientation, and of packaging them with containers of different types. In these cases, in addition to stopping production, it is necessary to replace the packaging machine entirely.

However, this solution is inadequate with the needs of the sector wherein high packaging flexibility is required in order to be able to provide consumers with various and different types of packages of absorbent sanitary articles.

Considering the case of a production machine connected to one or more packaging machines by means of a transport apparatus, an additional problem is also known which will be described below.

It is known that the absorbent sanitary articles made by the production machine are supplied in succession, or already grouped into groups, to special transport units which are positioned each time in a receiving area of the transport apparatus.

Once the group of absorbent sanitary articles has been received, each transport unit carries the respective group of absorbent sanitary articles to a delivery area of the transport apparatus, where the group is delivered to the packaging machine.

The timing with which the absorbent sanitary articles are produced, grouped, transported, delivered and packaged are suitably set so that there is a continuous cycle between the production machine and the packaging machine that allows maximizing production efficiency.

Due to the needs of the sector that impose ever faster systems to process an ever-increasing number of absorbent sanitary articles in a unit of time, it is common for some packages to be defective, or for some of the absorbent sanitary articles contained in these defective packages not to be included within the parameters of acceptability for marketing.

Although the absorbent sanitary articles contained in a package are free from imperfections, or in any case acceptable in relation to the acceptability parameters, it is frequent that they are rejected in bulk only due to some defects in the package such as the presence of cuts, incorrect or incomplete prints, wrinkles, incorrect or incomplete joints, or other imperfections.

Once the defective packaging has been removed, it is known that the absorbent sanitary articles contained therein are reinserted into the transport apparatus in order to be packaged again.

These article re-insertion operations, also referred to in the sector as re-pack operations, as well as other similar operations wherein an additional article is to be added, such as the addition of an advertising sheet to the group of articles to be packaged, require that at least the production machine is not running.

To avoid having to interrupt production for each individual package deemed defective, it is known that defective packages are accumulated near the transport apparatus, or stored in special warehouses.

In addition to requiring large spaces near the transport apparatus, or special warehouse spaces, the accumulation of defective packages requires the use of multiple operators and, moreover, the accumulated packages may be an obstacle for carrying out many operations during production.

The re-pack operations require the use of multiple operators who could be used in other operations, such as maintenance operations, or format-change operations, such as changing the settings of the production machine and/or the packaging machine.

Some known solutions envisage that these re-pack operations are carried out while the production machine operates with a lower production rate than the normal production rate. For example, it is possible to set some transport units so that they are not filled in the receiving area, but manually by an operator along the route.

In addition to representing a serious danger for operators, these known solutions are slow and do not allow the production machine to operate at its maximum production rate, which leads to a significant reduction in the number of absorbent sanitary articles that can be produced in the unit of time Similar problems are also encountered in the case of carrying out maintenance operations on the transport units for which it is—in any case—necessary to interrupt the production and packaging of the absorbent sanitary articles.

In this context, despite the efforts made by experts in the sector, an efficient solution is not yet available that allows carrying out of re-pack operations or other similar operations wherein it is not necessary to interrupt or slow down the production of absorbent sanitary articles.

There is, therefore, a need to improve and make a plant available for packaging groups of absorbent sanitary articles, as well as a method for managing a plant for packaging groups of absorbent sanitary articles which overcomes at least one of the drawbacks of the prior art.

There is also the need to improve and make an apparatus available for transporting absorbent sanitary articles that allows a production machine to be functionally connected to one or more packaging machines, as well as a transport method which overcomes at least one of the drawbacks of the prior art.

One object of the present invention is to provide a plant for packaging groups of absorbent sanitary articles that is flexible and that allows processing of various and different groups of absorbent sanitary articles quickly in relation to the specific batches to be packaged.

Another object of the present invention to provide a plant for packaging groups of absorbent sanitary articles that does not require long and laborious modifications to the plant, or the use of operators, to package groups of absorbent sanitary articles comprising different articles and/or groups with different numbers of absorbent sanitary articles.

Another object of the present invention is to provide a method for managing a packaging plant that allows the plant to be managed efficiently so as to obtain various customized packages quickly, without the need to interrupt production for a long time, and without the use of operators for manual packaging.

One object of the present invention is to provide an apparatus for transporting absorbent sanitary articles that is capable of managing said absorbent sanitary articles to produce a plurality of packages each having a desired number of absorbent sanitary articles, even very different from each other.

It is also an object of the present invention to provide an apparatus for transporting absorbent sanitary articles that allows managing these absorbent sanitary articles in order to be able to modify the number of absorbent sanitary articles to be packaged without the need to stop production.

A further object of the present invention is to provide a transport apparatus that allows managing a plurality of absorbent sanitary articles made by the production machine, even at the maximum production rate at which the latter is able to operate.

Another object of the present invention to provide a transport apparatus of absorbent sanitary articles capable of managing these absorbent sanitary articles to make different packages by means of different packaging machines, even simultaneously, ensuring production continuity.

Another object of the present invention is to provide a method for transporting absorbent sanitary articles capable of managing these absorbent sanitary articles to package them in special packaging machines, while maintaining production continuity, and also maximizing the number of absorbent sanitary articles that can be produced in a reference time.

An object of the present invention is to provide an apparatus for transporting absorbent sanitary articles which is able to operate while maintaining production continuity, and which—at the same time—allows re-pack operations to be carried out without slowing down production.

Another object of the present invention to provide a transport apparatus for absorbent sanitary articles that is safe for the operators and that allows operators to carry out re-pack operations even for each single package considered defective, without the need to store them.

The present Applicant has devised, tested and implemented this invention to overcome the drawbacks of the prior art and to obtain these and additional objects and advantages.

SUMMARY OF THE INVENTION

The present invention is expressed and characterized in the independent claims, while the dependent claims set out other characteristics of the present invention or variants of the idea of the main solution.

In accordance with the aforesaid objects, possible embodiments of the present invention relate to a packaging plant of groups of absorbent sanitary articles comprising one or more machines for producing groups of absorbent sanitary articles, packaging machines for groups of absorbent sanitary articles, and a transport apparatus functionally connected to the production machine(s) and to the packaging machines.

The transport apparatus is configured to transport the groups of absorbent sanitary articles from the production machine(s) to the packaging machines in the desired order.

The transport apparatus allows connection of each of the one or more production machines to the desired packaging machines, which—in this way—can automatically process and package different combinations of groups of absorbent sanitary articles each time.

According to possible embodiments, the packaging plant comprises a first number of production machines, wherein the first number is equal to or greater than one.

In accordance with possible embodiments, the packaging plant comprises a second number of packaging machines, wherein the second number is equal to or greater than two.

According to possible embodiments, each of the packaging machines is configured to form a desired combination of groups of absorbent sanitary articles.

For example, a first packaging machine may form a first combination comprising three groups of absorbent sanitary articles of one type and two groups of absorbent sanitary articles of another type, while a second packaging machine may form a second combination comprising five groups of absorbent sanitary articles of one type and three groups of absorbent sanitary articles of another type.

The combinations that are formed by the various packaging machines can be set each time in relation to the batches to be produced.

Here and below, "combination of groups of absorbent sanitary articles" means an assembly of groups of absorbent sanitary articles comprising a number and/or types of absorbent sanitary articles that are the same or different from each other.

In accordance with an aspect of the present invention, the transport apparatus comprises a guide assembly provided with at least two distinct guide circuits, physically separated and facing each other at least in one coupling tract, and a plurality of transport units each configured for transporting at least one of the groups of absorbent sanitary articles along a desired path defined by the guide circuits. Here and below "physically separated" means that the guide circuits are completely separated from each other and there is no physical connection between them. This allows the guide circuits to be moved easily to achieve the desired configuration without the need to physically disassemble and separate the various guide circuits.

According to possible embodiments, the transport units are configured to move and to stop in a desired position along a guide circuit.

In accordance with possible embodiments, the transport units are configured to pass from one guide circuit to another guide circuit facing each other in a coupling tract where the guide circuits are physically separated. In other words, there is an on-the-fly passage of the transport units between the two circuits, without them having to move along physical connecting portions as occurs in the prior art.

In accordance with possible embodiments, each of the transport units are configured to pass from one guide circuit to another guide circuit at the coupling tract where the guide circuits are physically separated.

This aspect allows the groups of absorbent sanitary articles to be transported by means of the transport units which can bring these groups to the desired packaging machine in relation to the specific combination to be produced.

According to possible embodiments, each of the packaging machines is functionally connected to at least one guide circuit.

The guide circuits face each other in the coupling tracts, so that the transport units can pass from one guide circuit to the other in order to reach the desired packaging machine.

This allows the groups of absorbent sanitary articles to be moved, making them also complete differentiated paths so that they are delivered to the desired packaging machine in the desired order.

In accordance with possible embodiments, each of the transport units comprises a body and a containment member connected to the body, and configured to contain at least one of the groups of absorbent sanitary articles.

According to possible embodiments, the body is provided with a first magnetic element configured to magnetically couple to one of the guide circuits, and with a second magnetic element, opposite to the first magnetic element, configured to magnetically couple to another of the guide circuits.

This aspect allows optimizing and speeding up the passage of the transport unit from one guide circuit to another guide circuit and does not require the presence of a physical connection between the guide circuits, which can therefore be physically separated. The magnetic coupling may take place between the magnetic element and a coupling surface of the guide circuit facing the magnetic element. This coupling surface can be suitably sized and designed to define the distance between the transport unit and the guide circuit.

According to possible embodiments, each of the transport units is configured to move along the guide circuit to which it is coupled.

In accordance with possible embodiments, the first magnetic element and the second magnetic element can be selectively activated so that said transport unit is coupled to one of the guide circuits in the coupling tract where the guide circuits are physically separated from each other.

This aspect allows the transport unit to be coupled to the desired guide circuit in the coupling tract and then to perform the exchange, or rather, the passage of the transport unit from one guide circuit to the other guide circuit coupled to it.

According to possible embodiments, the containment member may be connected to the body by means of a connecting member configured to rotate around a first rotation axis parallel to the direction of movement defined by the guide circuit.

The longitudinal development of the guide circuit defines the movement direction along which the transport units can move.

This aspect allows positioning of the group of absorbent sanitary articles by means of the containment member towards the outside of the guide circuit in the desired position around the longitudinal axis of the guide circuit.

This allows the group of absorbent sanitary articles to be positioned in relation to the receiving position of the absorbent sanitary articles coming from the production machine and to the delivery position with which they are delivered to the desired packaging machine.

In accordance with possible embodiments, the connecting member can be configured to rotate around a second rotation axis perpendicular to the direction of movement.

This aspect allows rotation and then orientation of the groups of absorbent sanitary articles according to the desired orientation so that they can be delivered in a defined and precise way according to production needs.

According to possible embodiments, the guide assembly comprises at least one distinct auxiliary guide circuit, physically separated and facing one of the guide circuits at least in one auxiliary coupling tract, and at least one auxiliary transport unit configured to carry one of the groups of absorbent sanitary articles and/or an additional article along a desired path defined by the guide circuits.

The auxiliary circuit is useful if production of a package is required comprising additional articles, or other particular articles, in addition to the groups of absorbent sanitary articles produced by the production machines.

In accordance with possible embodiments, the auxiliary transport unit is configured to pass from the auxiliary guide circuit to one of the guide circuits, and vice versa, at the auxiliary coupling tract where the auxiliary guide circuit and the guide circuit are physically separated, wherein the auxiliary transport unit is configured to stop in the auxiliary guide circuit and to proceed along the auxiliary guide circuit at a speed less than the speed of the auxiliary transport unit in the guide circuits.

The auxiliary transport unit may be configured substantially like the transport units.

Thanks to the specific configuration of the auxiliary transport unit that allows it to stop, or to proceed along the auxiliary guide circuit, the operator interacting with the transport unit can easily carry out the delivery operations at low intervals, and such as to meet the safety requirements.

The presence of this auxiliary guide circuit allows packaging additional articles to those typically made by production machines, without having to stop the production machines or the transport apparatus.

According to possible embodiments, at least one of the guide circuits comprises at least two guide portions placed at different heights and connected to each other by means of a connecting portion, wherein the transport unit is configured to pass from a guide portion to another guide portion along the connecting portion.

This aspect allows production of a guide apparatus that is functionally connected to production machines and/or packaging machines whose receiving areas and delivery areas are placed at different heights.

The transport units therefore traveling along the connecting portion transport the respective group of absorbent sanitary articles by means of the containment member from a first height to a second height.

In accordance with possible embodiments, the plant comprises a control and command unit configured to control the transport units in a coordinated manner, to bring the groups of absorbent sanitary articles into the packaging machines in the desired order relative to the desired combination of the groups of absorbent sanitary articles to be made in each of the packaging machines.

This control and command unit allows defining each time (even while the transport units are in operation) the path and travel time that each of them must complete in order to bring the desired groups of absorbent sanitary articles to the packaging machines in the desired order.

According to possible embodiments, the present invention also relates to a method for managing a packaging plant of groups of absorbent sanitary articles.

In accordance with possible embodiments, the method comprises:
  a setting step of the supply order of the groups of absorbent sanitary articles for each of the packaging machines;
  a supplying step of the groups of absorbent sanitary articles from one or more production machines to respective transport units;
  a transporting step of the groups of absorbent sanitary articles by means of the transport units towards the packaging machines;
  a delivery step of the groups of absorbent sanitary articles to the packaging machines according to the respective set supply order.

Thanks to this method, it is possible to guarantee high flexibility in the type of packages that can be produced, optimizing the delivery and production times of the packages in relation to the groups of absorbent sanitary articles produced each time by the production machines.

In accordance with possible embodiments, the supply step, the transporting step, and the delivery step can be carried out simultaneously in relation to groups of different absorbent sanitary articles.

According to possible embodiments, the method envisages that at least two production machines supply groups of absorbent sanitary articles of different numbers.

According to possible embodiments, the method envisages that at least two production machines supply groups of absorbent sanitary articles of different types.

In accordance with the aforesaid objects, possible embodiments relate to an apparatus for transporting absorbent sanitary articles comprising a guide assembly and a plurality of transport units.

According to possible embodiments, the guide assembly has a receiving area functionally connected to a production machine of absorbent sanitary articles, and a plurality of delivery areas each functionally connected to a respective packaging machine.

In accordance with possible embodiments, each transport unit is configured to receive the absorbent sanitary articles from the production machine in the receiving area and to transport them to one of the delivery areas along a desired path defined by the guide assembly.

In accordance with possible embodiments, the guide assembly comprises a primary guide circuit wherein the receiving area is present, and a plurality of secondary guide circuits, each provided with a respective delivery area and each distinct, physically separated and facing the primary guide circuit in a respective coupling tract.

In accordance with possible embodiments, each of the transport units are configured to pass from the primary guide circuit to one of the secondary guide circuit, and vice versa, at the coupling tract.

Thanks to the present invention, it is possible to simultaneously produce a plurality of packages that are different from each other, without interrupting production.

Indeed, while the production machine supplies the absorbent sanitary articles to one or more transport units, other transport units can go to the desired packaging machine in the desired order to make the desired package.

This allows packages of absorbent sanitary articles to be made that differ even by many units, and it is also possible to package the absorbent sanitary articles supplied by the production machine in the desired way.

The present invention allows the production machine to be used at maximum production capacity, since the transport units can travel along the desired path to deliver the absorbent sanitary articles to the desired packaging machine taking a desired time.

In other words, each transport unit can stop for a desired time, or proceed at a desired speed along the path defined by the transport apparatus.

The presence of a single primary guide circuit allows different assemblies of absorbent sanitary articles to be sorted in the desired order, each consisting of a desired number of absorbent sanitary articles, which also differ by many units.

In relation to the set delivery order, the transport units can pass from the primary guide circuit to the desired secondary guide circuit.

In accordance with possible embodiments, each of the transport units comprises a body and a containment member connected to the body and configured to contain a number of absorbent sanitary articles.

According to possible embodiments, the body is provided with a first magnetic element configured to magnetically couple to the primary magnetic guide circuit and with a second magnetic element, opposite to the first magnetic element, configured to magnetically couple to at least one of the secondary guide circuits.

This aspect allows optimizing and speeding up the passage of the transport unit from a primary guide circuit to the secondary guide circuit, and vice versa.

The magnetic coupling may take place between the magnetic element and a coupling surface of the primary guide circuit, or the secondary guide circuit facing the magnetic element.

This coupling surface can be suitably sized and designed to define the distance between the transport unit and the primary guide circuit or the secondary guide circuit.

According to possible embodiments, each of the transport units is configured to move or to stop along the primary guide circuit or along the secondary guide circuit to which it is coupled.

In accordance with possible embodiments, the first magnetic element and the second magnetic element can be selectively activated so that the transport unit is coupled to the primary guide circuit or to one of the secondary guide circuits in the coupling tract.

This aspect allows the transport unit to be coupled to the desired guide circuit in the coupling tract and then to perform the exchange, or rather, the passage of the transport unit from one guide circuit to the other guide circuit coupled to it.

According to possible embodiments, at least two of the secondary guide circuits have their respective delivery areas facing outwards of the secondary guide circuits along two directions parallel to each other.

This aspect makes it possible to position the packaging machines on the side, so as to subsequently be able to manage the packages made therefrom easily from a common side.

This simplifies the storage and shipping operations of the packages made, as they are located in a single area of the factory.

According to possible embodiments, at least two of the secondary guide circuits have their respective delivery areas facing outwards of the secondary guide circuits along two directions perpendicular to each other.

This aspect allows optimizing the available spaces in order to also use side spaces typically not used to contain the extension of the spaces used.

In other words, it is possible to contain the overall linear extension of the packaging plant by using transverse areas.

According to possible embodiments, at least two of the secondary guide circuits have their respective delivery areas facing outwards of the secondary guide circuits along two directions opposite to each other.

This aspect is particularly advantageous in cases where it is necessary to diversify the points of collection, storage, or shipment of the packages made.

In accordance with possible embodiments, the primary guide circuit has the receiving area where, during use, the absorbent sanitary articles are provided along a first direction facing towards the inside of the primary guide circuit, and at least one of the secondary guide circuits has the delivery area where, during use, the absorbent sanitary articles are delivered facing outwards of the secondary guide circuit along a second direction.

Thanks to the present invention and to the embodiments described so far, it is possible to group, manage and package a plurality of groups of different absorbent sanitary articles, providing the absorbent sanitary articles at a single receiving area.

According to possible embodiments, the primary guide circuit comprises a second receiving area functionally connected to the machine for producing absorbent sanitary articles.

This aspect allows optimizing the grouping of the absorbent sanitary articles so that, while a transport unit loaded with absorbent sanitary articles moves from the first receiving area, the production machine can simultaneously supply the absorbent sanitary articles to another transport unit in the second receiving area.

This allows operating at the maximum production rate without interrupting the operation of the apparatus.

In accordance with possible embodiments, the present invention also relates to a method for transporting absorbent sanitary articles implemented by means of a transport apparatus as in one of the embodiments according to the present invention.

According to possible embodiments, the transport method comprises:
a supplying step of absorbent sanitary articles from the production machine to the transport units in the receiving area, wherein each of the transport units carries a respective number of absorbent sanitary articles;
a setting step of the supply order of absorbent sanitary articles carried by the transport units for each of the packaging machines;
a transporting step of absorbent sanitary articles by means of the transport units towards the packaging machines;
a delivery step of absorbent sanitary articles to the packaging machines according to the respective supply order.

Thanks to this method, it is possible to guarantee high flexibility in the type of packages that can be produced, optimizing the delivery and production times of the packages, while ensuring production continuity.

In accordance with possible embodiments, the supply step envisages providing at least two transport units with a different number of absorbent sanitary articles.

According to possible embodiments, the supply step envisages providing at least two transport units with a different type of absorbent sanitary articles.

In accordance with the aforesaid objects, possible embodiments of the present invention relate to an apparatus for transporting absorbent sanitary articles comprising a guide assembly and a plurality of transport units.

According to possible embodiments, the guide assembly has at least one receiving area functionally connected to a production machine of absorbent sanitary articles, and at least one delivery area functionally connected to a respective packaging machine.

In accordance with possible embodiments, each transport unit is configured to receive the absorbent sanitary articles from the production machine in the receiving area and to transport them to the delivery area along a desired path defined by the guide assembly.

Each of the transport units is configured to move along the guide assembly and to stop for a desired time in a position of the guide assembly.

According to possible embodiments, the guide assembly comprises an inlet tract wherein the receiving area is present, an outlet tract wherein the delivery zone is present, an auxiliary inlet tract wherein an auxiliary receiving area is present, and a transit tract.

The auxiliary receiving area is suitable for carrying out re-pack operations or other similar operations wherein the supply of absorbent sanitary articles, or other articles such as advertising sheets, or other articles, is envisaged.

The transit tract is suitable for the transit of transport units and constitutes at least part of a path that can be traveled by the transport unit of the guide assembly.

In accordance with possible embodiments, the guide assembly comprises a first exchange assembly connected to the transit tract, to the auxiliary inlet tract and to the outlet tract.

According to possible embodiments, the first exchange assembly defines a first connection path between the transit tract and the outlet tract, which includes the auxiliary inlet tract, and a second connection path between the transit tract and the outlet tract, which does not include the auxiliary inlet tract.

In accordance with possible embodiments, the guide assembly comprises a second exchange assembly connected to the outlet tract, to the inlet tract and to the transit tract.

According to possible embodiments, the second exchange assembly defines a third connection path between the outlet tract and the transit tract, which includes the inlet tract, and a fourth connection path between the outlet tract and the transit tract which does not include the inlet tract.

Thanks to the present invention it is possible to carry out re-pack operations, or other similar operations in the auxiliary inlet tract, without the need to interrupt production.

The presence of the exchange assemblies allows optimizing the timings, allowing the production machine to operate at its maximum production rate.

The first exchange assembly defines two routes that can be traveled by the transport units in relation to the possibility of having to perform re-pack operations, maintenance on the transport units, or other similar operations.

The first path can be covered by one or more empty or partially full transport units, so that they are positioned at the auxiliary receiving area where an operator, or a special automatic system, carries out the re-pack operations.

These operations take place while the production machine is in operation, since the full transport units can travel the second path defined by the first exchange assembly without being hindered by the transport units present in the auxiliary inlet tract.

Once the re-pack operations have been carried out, the transport units to which the recovered absorbent sanitary articles have been supplied pass through the outlet tract by means of the first exchange assembly and enter the flow of transport units so as not to slow down the production flow.

The second exchange assembly turns out to be advantageous in terms of the performance of the transport apparatus, as it allows one or more empty transport units to be arranged, without the need for them to pass through the inlet tract.

The transit of the empty transport units in the inlet tract that will subsequently be positioned in the auxiliary inlet tract requires a transient wherein the production machine does not have to provide absorbent sanitary articles.

If the production machine is configured to supply absorbent sanitary articles with a defined frequency, the transit of an empty transport unit intended to be used for re-pack operations requires slowing down of the production machine speed to such an extent that the supply time between two successive articles is slower than the time necessary for a transport unit to pass through the receiving area, and for the subsequent transport unit to position itself in the receiving area to receive the absorbent sanitary articles from the production machine.

This limit is advantageously overcome thanks to the presence of the second transit assembly, which defines a path that does not include the inlet tract, and which allows a transport unit emptied in the delivery area to be able to reach the transit tract and, subsequently, the auxiliary inlet tract, without slowing or interrupting the supply of absorbent sanitary articles from the production machine.

Thanks to the presence of the second exchange assembly, it is possible to maintain production continuity by filling transport units continuously without interruptions, to allow a transport unit to pass through the receiving area without filling, for re-packing.

The combination of the first exchange assembly with the second exchange assembly is advantageous since the synergistic and combined effect of them allows optimizing the transport of the transport units in the guide assembly, even if it is necessary to carry out re-packing and maintenance operations, or other similar operations.

In accordance with possible embodiments, the guide assembly comprises a closed circuit wherein the transit tract and the outlet tract are present.

According to possible embodiments, the first exchange assembly comprises a first distinct exchange element, physically separated and facing the closed circuit and the auxiliary inlet tract, in a first coupling tract and in a second coupling tract, respectively.

According to possible embodiments, the first exchange assembly comprises a second distinct exchange element, physically separated and facing the closed circuit and the auxiliary inlet tract, in a third coupling tract and in a fourth coupling tract, respectively.

According to possible embodiments, the second exchange assembly comprises a third distinct exchange element, physically separated and facing the closed circuit and the inlet tract, in a fifth coupling tract and in a sixth coupling tract, respectively.

According to possible embodiments, the second exchange assembly comprises a fourth distinct exchange element, physically separated and facing the closed circuit and the inlet tract, in a seventh coupling tract and in an eighth coupling tract, respectively. This structural configuration allows the transport unit to alternatively complete the first connection path or the second connection path and, alternatively, the third connection path or the fourth connection path.

This structural configuration of the guide assembly allows maintaining the orientation of the transport units towards the outside of the transport apparatus in the outlet tract, in the inlet tract, in the transit tract, and in the auxiliary inlet tract, so that the transfer of absorbent sanitary articles to and from the transport units is easy.

According to possible embodiments, at least one of the transport units is configured to pass from the closed circuit to the first exchange element, from the first exchange element to the auxiliary inlet tract, from the auxiliary inlet tract to the second exchange element, from the second exchange element to the closed circuit, from the closed circuit to the third exchange element, from the third exchange element to the inlet tract, from the inlet tract to the fourth exchange element, and from the fourth exchange element to the closed circuit at the respective coupling tract.

This aspect makes it possible to transport the absorbent sanitary articles by means of the transport units, which can pass from one tract to another depending on the desired route to be taken.

In accordance with possible embodiments, the guide assembly comprises a closed circuit wherein a transit tract and the outlet tract are present.

According to possible embodiments, the first exchange assembly comprises a first distinct open circuit, physically separated and facing the closed circuit in a first inlet coupling tract, and in a first outlet coupling tract between which the auxiliary inlet tract is comprised.

According to possible embodiments, the second exchange assembly comprises a second distinct open circuit, physically separated and facing the closed circuit in a second inlet coupling tract, and in a second outlet coupling tract between which the inlet tract is comprised.

This structural configuration allows the transport unit to alternatively complete the first connection path or the second connection path and, alternatively, the third connection path or the fourth connection path.

This configuration allows limiting the number of elements of the guide assembly necessary to allow the transport units to complete the desired path.

According to possible embodiments, at least one of the transport units is configured to pass from the closed circuit to the first open circuit, and vice versa, at the first inlet coupling tract and at the first outlet coupling tract, respectively.

According to possible embodiments, at least one of the transport units is configured to pass from the closed circuit to the second open circuit, and vice versa, at the second inlet coupling tract and at the second outlet coupling tract, respectively.

According to possible embodiments, each of the transport units comprises a body and a containment member connected to the body and configured to contain the absorbent sanitary articles.

According to possible embodiments, the body is provided with a first magnetic element configured to magnetically couple to a portion of the guide assembly, and with a second magnetic element, opposite to the first magnetic element, configured to magnetically couple to another portion of the guide assembly.

This aspect makes it possible to optimize and speed up the passage of the transport unit from a portion of the guide assembly, or rather, from one of the tracts that make up the guide assembly, to another portion of the guide assembly, or rather to another of the tracts that make up the guide assembly. The magnetic coupling may take place between the magnetic element and a coupling surface of the guide assembly facing the magnetic element. This coupling surface may be suitably sized and designed to define the distance between the transport unit and the guide assembly.

According to possible embodiments, each of the transport units is configured to move along the tract of the guide assembly to which it is coupled.

In accordance with possible embodiments, the first magnetic element and the second magnetic element can be selectively activated so that the transport unit is coupled to a portion of the guide assembly in one of the coupling tracts.

This aspect allows the transport unit to be coupled to the desired tract of the guide assembly in the coupling tract and then to perform the exchange, or rather, the passage of the transport unit from one tract of the guide assembly to the other tract of the guide assembly coupled thereto.

According to possible embodiments, the containment member is connected to the body by means of a connecting member configured to rotate around a second rotation axis perpendicular to the direction of movement defined by the guide circuit.

The longitudinal development of the tract of the guide assembly defines the movement direction along which the transport units can move.

This aspect allows positioning the absorbent sanitary articles by means of the containment member towards the outside of the guide assembly in the desired position around the longitudinal axis of the guide circuit.

This allows the absorbent sanitary articles to be positioned in relation to the receiving position of the absorbent sanitary articles coming from the production machine, and to the delivery position with which they are delivered to the desired packaging machine.

In other words, the connecting member allows rotation of the containment member with respect to the second rotation axis so that the containment compartment defined by the containment member faces in the desired direction.

In accordance with possible embodiments, the guide circuit comprises at least one spiral tract wherein there is a first surface and a second surface, opposite to the first surface, arranged along a spiral path, so that leaving the spiral path the first surface and the second surface are inverted with each other.

This aspect allows minimizing the steps of the transport units by positioning the transport units towards the outside or towards the inside of the guide assembly.

According to possible embodiments, the receiving area faces the inside of the guide assembly along a first direction, and the delivery area faces the outside of the guide assembly along a second direction parallel to the first direction.

This aspect makes it possible to arrange the production machine and the packaging machine in an optimal way, so that operators can carry out the operations easily, and by locating the production and the packaging in two different and non-interfering areas of the plant.

In accordance with possible embodiments, the guide assembly comprises a plurality of delivery areas functionally connected to the packaging machine.

This aspect allows the simultaneous transfer of a plurality of absorbent sanitary articles so as to maximize the production capacity and significantly reduce the transfer time, since it is possible to position two or more transport units at the same time.

ILLUSTRATION OF THE DRAWINGS

Figure 13:
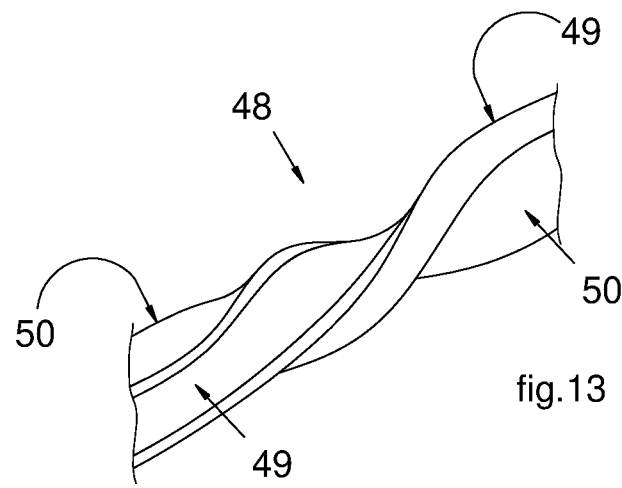

These and other characteristics of the present invention will become clear from the following description of embodiments, given as a non-limiting example, with reference to the attached drawings wherein:

FIG. 1 schematically illustrates a packaging plant according to a possible embodiment of the present invention;

FIG. 2 schematically illustrates a detail of a transport apparatus according to a possible embodiment of the present invention;

FIG. 3 schematically illustrates a transport unit according to a possible embodiment of the present invention;

FIGS. 4 and 5 schematically illustrate two details of two possible embodiments of a guide circuit according to the present invention;

FIG. 6 schematically illustrates a packaging plant according to a possible embodiment of the present invention;

FIGS. 7-12 schematically illustrate possible embodiments of a transport apparatus according to the present invention;

FIG. 13 schematically illustrates a detail of a guide circuit according to a possible embodiment of the present invention;

FIG. 14 schematically illustrates a packaging plant according to a possible embodiment of the present invention;

FIGS. 15 and 16 schematically illustrate two possible embodiments of a movable device according to the present invention; To facilitate understanding, identical reference numbers have been used, where possible, to identify identical common elements in the Figures. It should be under-

DESCRIPTION OF THE EMBODIMENTS

Embodiments described here, with reference to FIGS. 1-6 and others, refer to a packaging plant 100 of groups G1, G2, G3 of absorbent sanitary articles including some details and to a method for managing a packaging plant 100.

Figure 7:
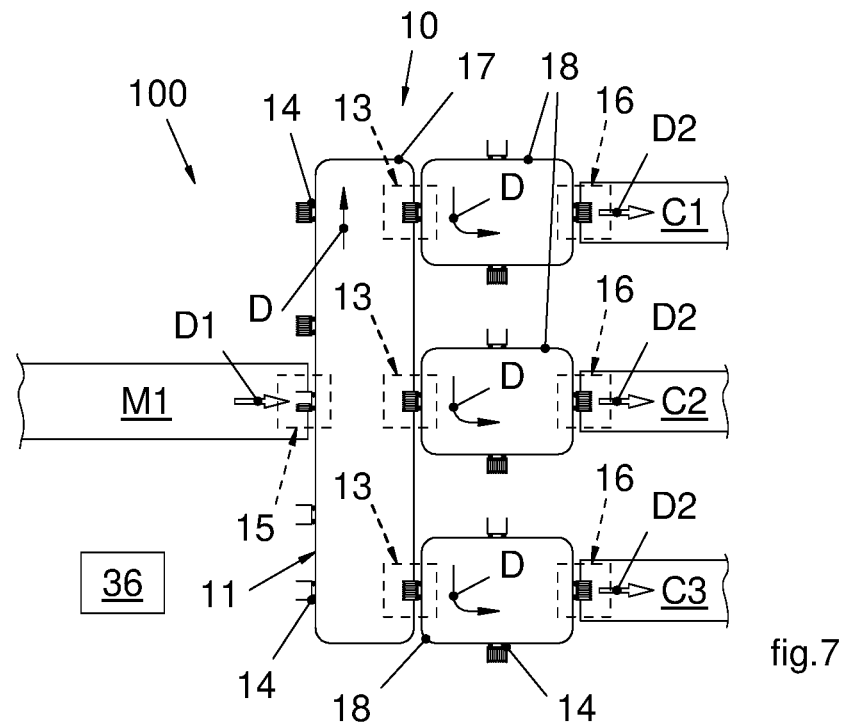
Figure 8:
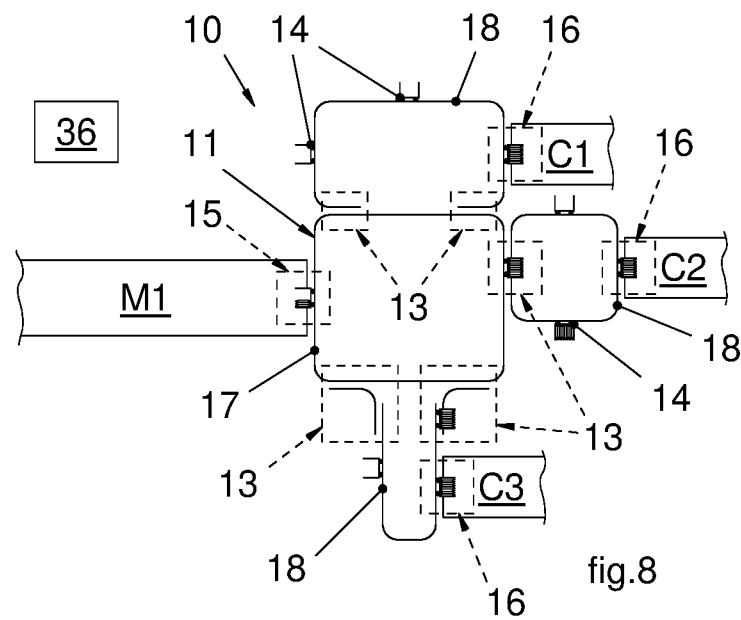
Figure 9:
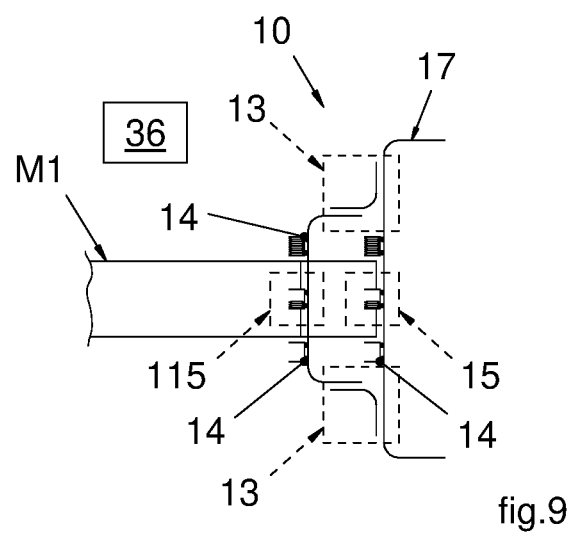

Additional embodiments described here, with reference to FIGS. 7-9 and others, refer to a transport apparatus 10 for absorbent sanitary articles and to a method for transporting relative absorbent sanitary articles.

Figure 10:
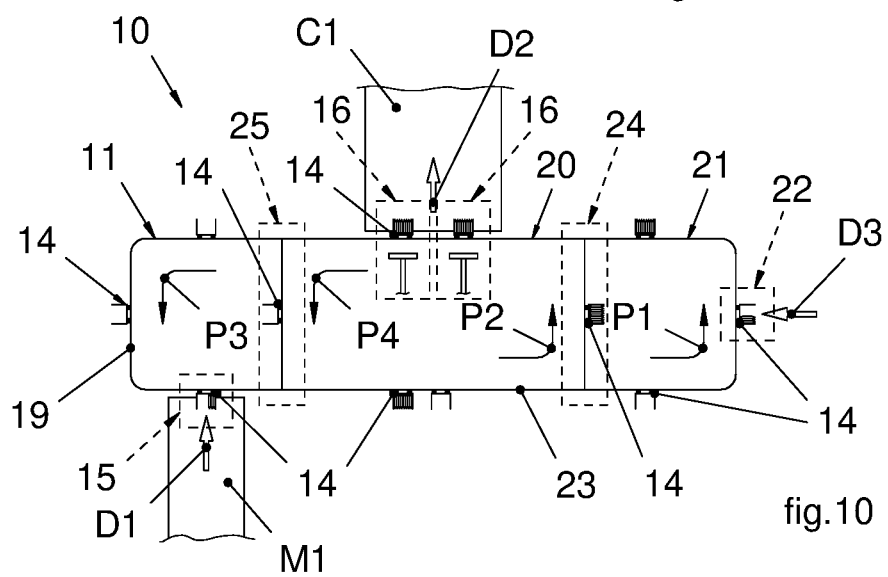
Figure 11:
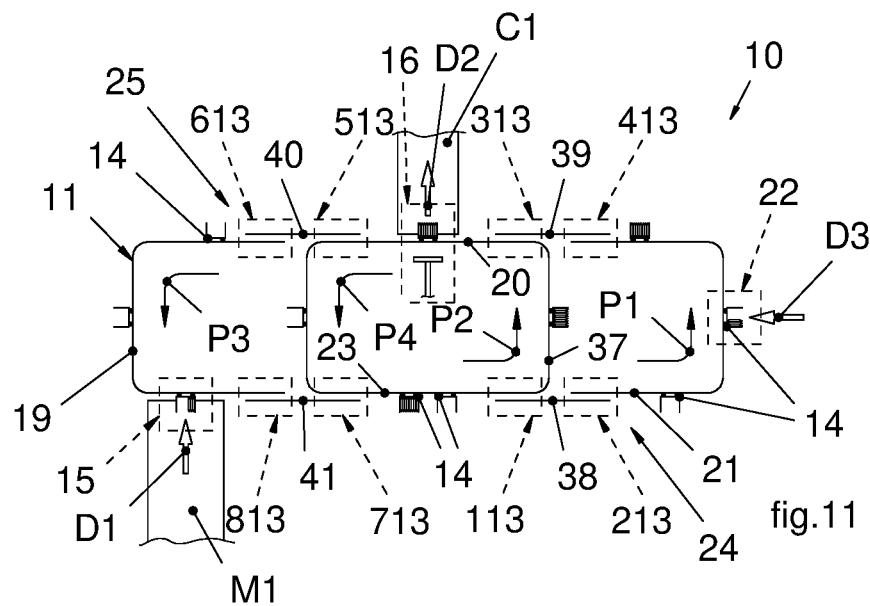
Figure 12:
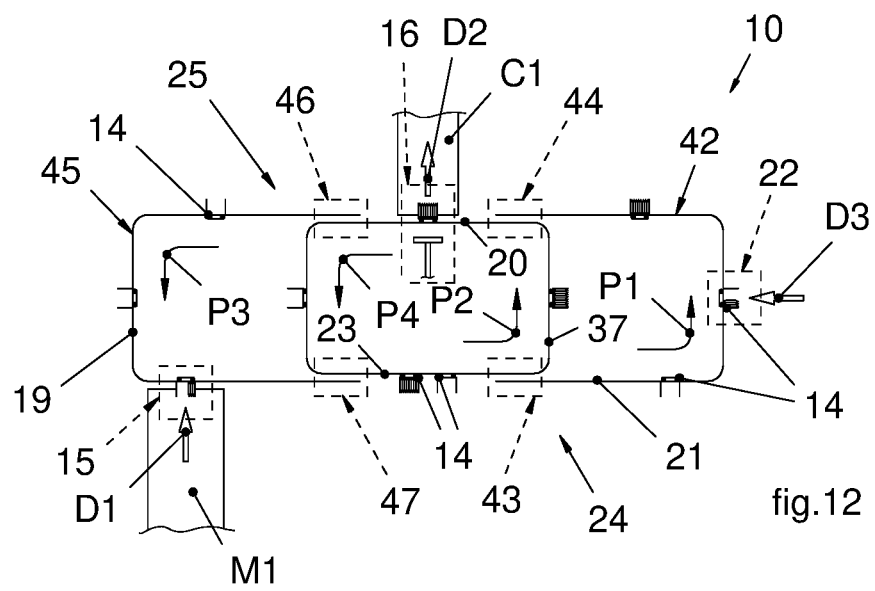

Other embodiments described here, with reference to FIGS. 10-12 and others, refer to an apparatus 10 for transporting absorbent sanitary articles suitably designed to manage possible insertions of absorbent sanitary articles coming from non-compliant packages, or of particular absorbent sanitary articles, or other articles to be combined with already formed groups of absorbent sanitary articles.

Embodiments described here, with reference to FIGS. 14-16 and others, refer to a movable device 90 for transporting groups G1, G2, G3 of articles in a packaging plant 100, and to a packaging plant 100 comprising a plurality of these movable devices 90.

According to possible embodiments, the packaging plant 100 of groups G1, G2, G3 of absorbent sanitary articles comprises a first number N1 of production machines M1, M2, M3 of groups G1, G2, G3 of absorbent sanitary articles.

In accordance with possible embodiments, the production machines M1, M2, M3 may be configured to produce the same or different types of absorbent sanitary articles.

According to possible embodiments, one or more production machines M1, M2, M3 may be configured to produce absorbent sanitary articles with different or identical properties and/or components.

In accordance with possible embodiments, at least one of the production machines M1, M2, M3 may be configured to produce groups G1, G2, G3 of absorbent sanitary articles of one type, and at least one other of the production machines M1, M2, M3 can be configured to produce groups G1, G2, G3 of absorbent sanitary articles of another type.

For example, the two groups of absorbent sanitary articles of different types may have two different sizes.

According to possible embodiments, at least two production machines M1, M2, M3 may be arranged in the packaging plant 100 so that the release of the absorbent sanitary articles is oriented towards a common release direction.

In accordance with possible embodiments, at least two production machines M1, M2, M3 may be arranged in the packaging plant 100 so that the release of the absorbent sanitary articles is oriented in the opposite direction towards a common area of the packaging plant 100.

In accordance with possible embodiments, at least two production machines M1, M2, M3 may be arranged in the packaging plant 100 so that the respective release directions of the absorbent sanitary articles are perpendicular to each other towards a common area of the packaging plant 100.

In accordance with possible embodiments, at least two production machines M1, M2, M3 may be configured to supply the absorbent sanitary articles at different heights, wherein each height is defined with respect to a common horizontal reference.

For example, if two production machines M1, M2, M3 are arranged at different areas of the packaging plant 100 wherein the respective support surfaces have a difference in height, the height of each production machine M1, M2, M3 at which absorbent sanitary articles are supplied is defined, for example, in relation to the support surface of one of the two production machines M1, M2, M3.

In accordance with possible embodiments, at least two production machines M1, M2, M3 may be configured to supply the absorbent sanitary articles at the same height, wherein each height is defined with respect to a common horizontal reference.

According to possible embodiments, the first number N1 is equal to or greater than one.

According to possible embodiments, the packaging plant 100 comprises a second number N2 of packaging machines C1, C2, C3 of groups G1, G2, G3 of absorbent sanitary articles.

According to possible embodiments, the packaging machines C1, C2, C3 are configured to form a desired combination of groups G1, G2, G3 of absorbent sanitary articles.

The combination may include groups G1, G2, G3 of identical or different absorbent sanitary articles, both from the point of view of the number of absorbent sanitary articles present in the group G1, G2, G3, and from the point of view of the type of absorbent sanitary articles in the same group G1, G2, G3 or between distinct groups G1, G2, G3, as well as from the combined point of view of number and type.

According to possible embodiments, the packaging machine C1, C2, C3 may be configured to produce a customized package containing the desired combination.

In accordance with possible embodiments, the customized package may comprise a flexible packaging, a rigid cardboard or other type of flexible, or rigid packaging, in relation to the packaging and transport requirements.

According to possible embodiments, at least two packaging machines C1, C2, C3 can be arranged in the packaging plant 100 so that the receiving of groups G1, G2, G3 of absorbent sanitary articles is oriented towards a common receiving direction.

According to possible embodiments, at least two packaging machines C1, C2, C3 can be arranged in the packaging plant 100 so that the receiving of groups G1, G2, G3 of absorbent sanitary articles is oriented in the opposite direction towards a common area of the packaging plant 100.

According to possible embodiments, at least two packaging machines C1, C2, C3 can be arranged in the packaging plant 100 so that the respective directions of receiving the groups G1, G2, G3 of absorbent sanitary articles are perpendicular to each other towards a common area of the packaging plant 100.

In accordance with possible embodiments, at least two packaging machines C1, C2, C3 can be configured to receive the groups G1, G2, G3 of absorbent sanitary articles at different heights, wherein each height is defined with respect to a common horizontal reference.

For example, if two packaging machines C1, C2, C3 are arranged at different areas of the packaging plant 100 wherein the respective support surfaces have a difference in height, the height of each packaging machine C1, C2, C3 at which groups G1, G2, G3 of absorbent sanitary articles are received is defined, for example, in relation to the support surface of one of the two packaging machines M1, M2, M3.

In accordance with possible embodiments, at least two packaging machines C1, C2, C3 can be configured to receive the groups G1, G2, G3 of absorbent sanitary articles at a common height, wherein each common height is defined with respect to a common horizontal reference.

In accordance with possible embodiments, at least one production machine M1, M2, M3 and one packaging machine C1, C2, C3 can be configured, respectively, to supply and to receive the groups G1, G2, G3 of absorbent sanitary articles at different heights, wherein each height is defined with respect to a common horizontal reference.

In accordance with possible embodiments, at least one production machine M1, M2, M3 and one packaging machine C1, C2, C3 can be configured, respectively, to supply and to receive the groups G1, G2, G3 of absorbent sanitary articles at a common height, wherein each common height is defined with respect to a common horizontal reference.

According to possible embodiments, the second number N2 is equal to or greater than two.

According to possible embodiments, the packaging plant 100 comprises a transport apparatus 10 functionally connected to the first number N1 of production machines M1, M2, M3 and to the second number N2 of packaging machines C1, C2, C3.

Here and below, "functional connection" means a connection between two components of the packaging plant 100 configured to create a continuous process of production, transport and packaging of the groups G1, G2, G3 of absorbent sanitary articles.

The functional connection can be produced by suitable transfer means configured to transfer and to form groups G1, G2, G3 of absorbent sanitary articles. For example, the transfer means may comprise pushers, manipulators, robots, conveyor belts, or the like.

In accordance with possible embodiments, each of the one or more production machines M1, M2, M3 is functionally connected to the transport apparatus 10 at respective receiving areas 15, wherein the absorbent sanitary articles produced by the respective production machine M1, M2, M3 are supplied.

According to possible embodiments, each of the packaging machines C1, C2, C3 is functionally connected to the transport apparatus 10 at respective delivery areas 16, wherein the absorbent sanitary articles are delivered to the respective packaging machine C1, C2, C3.

In accordance with possible embodiments, the transport apparatus 10 is configured to transport the groups G1, G2, G3 of absorbent sanitary articles from the production machine(s) M1, M2, M3 to the packaging machines C1, C2, C3 in the desired order.

According to possible embodiments, the transport apparatus 10 comprises a guide assembly 11 and a plurality of transport units 14.

According to possible embodiments, the guide assembly 11 may be provided with at least two distinct guide circuits 12, physically separated and facing each other at least in one coupling tract 13.

According to possible embodiments, each of the guide circuits 12 can be shaped so as to each define its own direction of movement D.

In accordance with possible embodiments, in the coupling tract 13, the guide circuits 12 facing each other have their respective directions of movement D substantially parallel to each other.

According to possible embodiments, at least one of the guide circuits 12 is functionally connected to at least one production machine M1, M2, M3 by means of at least one receiving area 15.

According to possible embodiments, at least one of the guide circuits 12 is functionally connected to at least one packaging machine C1, C2, C3 by means of at least one delivery area 16.

In accordance with possible embodiments, the guide circuit 12 may comprise a plurality of elements connected together to form the desired path.

In accordance with possible embodiments, at least one of the guide circuits 12 may define a closed path.

According to possible embodiments, at least one of the guide circuits 12 may define an open path.

According to possible embodiments, the coupling between at least two guide circuits 12 can be obtained by means of a distinct intermediate coupling element, physically separated and facing a guide circuit 12 in a first intermediate coupling tract and to another guide circuit 12 in a second intermediate coupling tract.

In accordance with possible embodiments, the coupling between at least two guide circuits 12 may be obtained by means of a plurality of intermediate coupling elements coupled together, wherein at least one intermediate coupling element is distinct, physically separated and facing a guide circuit 12 in an intermediate coupling tract, and at least one other intermediate coupling element is distinct, physically separated and facing another guide circuit 12 in another intermediate coupling tract.

According to possible embodiments, the elements present in the guide circuit 12 may have a solid shape having two surfaces 49 and 50 opposite each other and configured to make the coupling with the transport units 14.

In accordance with possible embodiments, the elements present in the guide circuit 12 may have a solid shape which extends along the direction of movement D.

According to possible embodiments, at least part of the elements present in the guide circuit 12 may have a solid shape defining a linear tract.

According to possible embodiments, at least part of the elements present in the guide circuit 12 may have a solid shape defining a curved tract.

In accordance with possible embodiments, at least one of the guide circuits 12 may comprise at least two guide portions 34 located at different heights H1 and H2 and connected to each other by means of a connecting portion 35.

In accordance with possible embodiments, the heights H1 and H2 relate to a common geometric plane of horizontal reference. For example, the geometric reference plane may coincide with the ground.

According to possible embodiments, the transport unit 14 may be configured to pass from a guide portion 34 to another guide portion 34 along the connecting portion 35.

In accordance with possible embodiments, the guide circuit 11 may comprise at least one spiral tract 48 wherein there is a first surface 49 and a second surface 50, opposite to the first surface 49, arranged along a spiral path, so that upon leaving the spiral path the first surface 49 and the second surface 50 are inverted with each other.

In accordance with possible embodiments, each of the transport units 14 can be configured to transport at least the groups G1, G2, G3 of absorbent sanitary articles along a desired path defined by the guide circuits 12.

For example, the desired path may comprise tracts of one or more guide circuits 12, even repeated so that a transport unit 14 travels the same tract of the guide circuit 12 several times.

According to possible embodiments, each transport unit 14 is configured to move along the desired path independently from the other transport units 14.

According to possible embodiments, each transport unit 14 is configured to stop at a guide circuit to which it is coupled.

According to possible embodiments, the movement and/or stopping along the guide circuit 12 can be obtained by means of magnetic movement means, aerostatic movement means, combinations thereof, or other means. For example, the movement may be substantially obtained as in linear magnetic motors.

According to possible embodiments, two or more transport units 14 may be configured to jointly transport one or more groups G1, G2, G3 of absorbent sanitary articles.

According to possible embodiments, a first transport unit 14 may be configured to transport a group G1, G2, G3 of absorbent sanitary articles and a second transport unit 14 may be configured to proceed at least for a tract along the same path followed by the first transport unit 14.

In this exemplary and non-limiting case, the second transport unit 14 may comprise retaining means configured to hold the group G1, G2, G3 of absorbent sanitary articles in position on the first transport unit 14.

For example, the retaining means of the second transport unit 14 may comprise a plate, pincers, or other retaining elements, which can be positioned at the first transport unit 14 so as to prevent the groups G1, G2, G3 from falling from the first transport unit 14.

According to possible embodiments, two or more transport units 14 may be configured to proceed in a coordinated manner at least for a tract along the same path of the guide assembly 11.

According to possible embodiments, each of the transport units 14 are configured to pass from one of the guide circuits 12 to another guide circuit 12, and vice versa, at the coupling tract 13.

According to possible embodiments, each of the transport units 14 may comprise a body 26 and a containment member 27 connected to the body 26.

In accordance with possible embodiments, the containment member 27 is configured to contain at least one group G1, G2, G3 of absorbent sanitary articles.

According to possible embodiments, the containment member 27 defines a containment compartment capable of containing a desired number of absorbent sanitary articles to form a group G1, G2, G3 of said articles.

In accordance with possible embodiments, the containment member 27 can be configured to define the desired containment compartment each time.

According to possible embodiments, the containment member 27 may comprise containment walls defining the containment compartment.

In accordance with possible embodiments, the containment walls can be positioned in the desired position so as to define, each time, the size of the containment compartment and therefore the number of absorbent sanitary articles of the group G1, G2, G3 to be transported.

In accordance with possible embodiments, the containment member 27 may be provided with retaining means designed to hold the group G1, G2, G3 of absorbent sanitary articles in position.

According to possible embodiments, the containment member 27 may be provided with one or more sensors designed to detect one or more pieces of information relating to the group G1, G2, G3 of absorbent sanitary articles that it contains. For example, the sensors may detect the type, position, weight, number or other parameters relating to the individual absorbent sanitary articles and/or to the group G1, G2, G3.

According to possible embodiments, the containment member 27 may be connected to the body 26 by means of a connecting member 30 configured to rotate around a rotation axis X1 parallel to the direction of movement D defined by the guide circuit 12.

This allows rotation of the containment organ 27 around the rotation axis X1 and then to position it in the desired way with respect to the rotation axis X1.

According to possible embodiments, the transport unit 14 may comprise positioning means configured to position the containment member 27 with respect to the body 26.

For example, the positioning means can position the containment member 27 at a desired height.

According to possible embodiments, the connecting member 30 may be configured to rotate around a second rotation axis X2 perpendicular to the direction of movement D.

This allows orienting the containment organ towards the desired direction perpendicular to the second rotation axis X2.

According to possible embodiments, the body 26 is provided with a first magnetic element 28 configured to magnetically couple to one of the guide circuits 12, and with a second magnetic element 29, opposite to the first magnetic element 28, configured to magnetically couple to another guide circuit 12.

According to possible embodiments, the first magnetic element 28 and the second magnetic element 29 can be selectively activated so that the transport unit 14 is coupled to one of the guide circuits 12 in the coupling tract 13.

In accordance with possible embodiments, the first magnetic element 28 and/or the second magnetic element 29 may comprise one or more magnets.

According to possible embodiments, the magnets may be operated by means of a source of electrical energy.

In accordance with possible embodiments, each of the transport units 14 may be provided with movement means configured to move the transport unit 14 along the guide circuit 12 to which it is coupled.

For example, the magnetic elements 28 and 29 may also be configured to move the transport unit 14 along the guide circuit 12.

According to possible embodiments, the movement means are configured to be operated remotely, for example, from a terminal.

In accordance with possible embodiments, the movement means may be included in the guide circuit 12.

According to possible embodiments, the transport unit 14 is configured to stop at an area of the guide assembly 11.

In accordance with possible embodiments, the transport unit 14 may be provided with auxiliary movement means 62 joined to the guide circuit 12 to facilitate the guide and support of the transport unit 14 on the guide circuit 12.

For example, the auxiliary movement means 62 may comprise a pair of wheels spaced apart along the longitudinal development of the body 26 of the transport unit 14 which, while the transport unit 14 is coupled to a guide circuit 12, are configured to rotate along a guide path, not illustrated, defined by the coupling surface of the guide circuit 12.

In other words, once the pair of wheels 62 is coupled to the coupling surface, for example, by means of guide rails, or by means of suitable protrusions of the coupling surface, defining the guide path, the transport unit 14 is stably coupled to the guide circuit 12.

In accordance with possible embodiments, the guide assembly 11 may comprise at least one distinct auxiliary guide circuit 31, physically separated and facing one of the guide circuits 12 at least at a coupling tract 32, and at least one auxiliary transport unit 33.

According to possible embodiments, the auxiliary transport unit 33 can be configured substantially like the transport units 14.

In accordance with possible embodiments, the auxiliary transport units 33 may be configured to transport one of the groups G1, G2, G3 of absorbent sanitary articles and/or an additional article along a desired path defined by the guide circuits 12.

In accordance with possible embodiments, the auxiliary transport unit 33 is configured to pass from the auxiliary guide circuit 31 to one of the secondary guide circuits 12, and vice versa, at the auxiliary coupling tract 32.

In accordance with possible embodiments, the auxiliary transport unit 33 is configured to stop in the auxiliary guide circuit 31 and to proceed along the auxiliary guide circuit 31 at a speed lower than the speed of the auxiliary transport unit 33 in the guide circuits 12.

This allows the operator to act safely while interacting with the auxiliary transport unit 33, as the speed of the latter is limited or even zero in the guide circuit 31.

According to possible embodiments, the transport unit 14 can be configured as the auxiliary transport unit 33 so as to be able to stop or proceed along the auxiliary guide circuit 31 at a lower speed than the transport unit 14 in the guide circuits 12.

The auxiliary guide circuit 31 is useful for inserting absorbent sanitary articles or other articles into the transport cycle to be joined to the groups G1, G2, G3 of absorbent sanitary articles in order to create further customized packages.

Thanks to the auxiliary guide circuit 31, it is possible to insert articles into the transport cycle without interrupting the production of the articles.

According to possible embodiments, the transport units 14 can be configured to pass from a guide circuit 12 to the auxiliary guide circuit 31 at the coupling tract 32.

In this way, the auxiliary guide circuit 31 may also be useful for carrying out maintenance operations on the transport units 14.

According to possible embodiments, the packaging plant 100 comprises a control and command unit configured to control the transport units 14 in a coordinated manner to bring the groups G1, G2, G3 of absorbent sanitary articles into the packaging machines C1, C2, C3 in the desired order in relation to the desired combination of the groups G1, G2, G3 of absorbent sanitary articles to be made in each of the packaging machines.

For example, the control and command unit 36 may be fixed to one of the production machines M1, M2, M3, to one of the packaging machines C1, C2, C3, to the guide assembly 11, or it can be a portable component. The control and command unit 36 may include any of the following components: a computer, circuitry, a tablet, a smartphone, a programmable controller, and their combinations.

According to possible embodiments, the control and command unit 36 is configured to receive a signal comprising information on the combinations of groups G1, G2, G3 to be created, to set the path to be covered and the stop times for each transport unit 14, to bring the groups G1, G2, G3 into the order desired from the production machines M1, M2, M3 to the packaging machines C1, C2, C3.

In accordance with possible embodiments, the control and command unit 36 is configured to modify the paths and travel times in relation to an additional signal including information on a further combination of groups G1, G2, G3 that is to be created.

According to possible embodiments, the travel times and paths can be determined in relation to the specific production rates and the packaging times of the packaging machines C1, C2, C3.

In accordance with possible embodiments, the control and command unit 36 may be advantageously configured to receive signals from the individual transport units 14 and/or from sensors positioned in the packaging plant 100, so that it can control the transport units 14 in relation to the signals received, without them hindering each other and in order to optimize the times and paths of each transport unit to bring the groups G1, G2, G3 of absorbent sanitary articles quickly to the packaging machines C1, C2, C3.

According to possible embodiments, the signals may comprise the position in the guide assembly 11 of the desired transport unit 14.

According to possible embodiments, the present invention also relate to a method for managing a packaging plant 100.

According to possible embodiments, the method comprises:
- a setting step of the supply order of the groups G1, G2, G3 of absorbent sanitary articles for each of said packaging machines C1, C2, C3;
- a supplying step of the groups G1, G2, G3 of absorbent sanitary articles from one or more production machines M1, M2, M3 to respective transport units 14;
- a transporting step of the groups G1, G2, G3 of absorbent sanitary articles by means of the transport units 14 towards the packaging machines C1, C2, C3;
- a delivery step of the groups G1, G2, G3 of absorbent sanitary articles to said packaging machines C1, C2, C3 according to the respective set supply order.

According to possible embodiments, the management method envisages that at least two of the production machines M1, M2, M3 supply groups G1, G2, G3 of absorbent sanitary articles of different numbers.

According to possible embodiments, the management method envisages that at least two of the production machines M1, M2, M3 supply groups G1, G2, G3 of absorbent sanitary articles of different types.

In accordance with possible embodiments, the apparatus 10 for transporting absorbent sanitary articles comprises a guide assembly 11 and a plurality of transport units 14.

According to possible embodiments, the guide assembly 11 may present at least one receiving area 15 functionally connected to a production machine M1 of absorbent sanitary articles and a plurality of delivery areas 16, each functionally connected to a respective packaging machine C1, C2, C3.

According to possible embodiments, each transport unit 14 may be configured to receive absorbent sanitary articles from the production machine M1 in the receiving area 15 and to transport them to one of the delivery areas 16 along a desired path defined by the guide assembly 11.

In accordance with possible embodiments, the guide assembly 11 may comprise a primary guide circuit 17 wherein the receiving area 15 is present, and a plurality of secondary guide circuits 18, each provided with a respective delivery area 16 and each distinct, physically separated and facing the primary guide circuit 17 in a respective coupling tract 13.

In accordance with possible embodiments, the transport units may be configured to pass from the primary guide circuit 17 to one of the secondary guide circuits 18, and vice versa, at the coupling tract 13.

The transport apparatus 10 allows functionally connecting a production machine M1 of absorbent sanitary articles to multiple packaging machines C1, C2, C3 so as to be able to create even different combinations of absorbent sanitary articles, in relation to the needs of the consumers.

Thanks to the transport apparatus 10, it is possible to create customized packages with various combinations of absorbent sanitary articles in parallel, and without interrupting the production flow of the production machine M1.

For example, it is possible to set one of the packaging machines C1, C2, C3 for producing a first package containing a first combination of absorbent sanitary articles and another of the packaging machines C1, C2, C3 for producing a second package containing a second combination of absorbent sanitary articles.

The transport apparatus 10 is considerably more advantageous than known solutions which envisage storing the absorbent sanitary articles to subsequently package them manually in relation to the orders received.

According to possible embodiments, the coupling between the primary guide circuit 17 and the secondary guide circuit 18 can be obtained by means of a distinct intermediate coupling element, physically separated and facing a primary guide circuit 17 in a first intermediate coupling tract and to the secondary guide circuit 18 in a second intermediate coupling tract.

In accordance with possible embodiments, the coupling between the primary guide circuit 17 and the secondary guide circuit 18 may be obtained by means of a plurality of intermediate coupling elements coupled together, wherein at least one intermediate coupling element is distinct, physically separated and facing the primary guide circuit 17 in an intermediate coupling tract, and at least one other intermediate coupling element is distinct, physically separated and facing the secondary guide circuit 18 in another intermediate coupling tract.

In accordance with possible embodiments, the primary guide circuit 17 and/or the secondary guide circuit 18 may comprise a plurality of elements connected together to form the desired path.

According to possible embodiments, the elements present in the primary guide circuit 17 and/or in the secondary guide circuit 18 may be substantially configured as the elements of the guide circuit 12.

In accordance with possible embodiments, at least one primary guide circuit 17 may define a closed path.

According to possible embodiments, at least one primary guide circuit 17 may define an open path.

In accordance with possible embodiments, at least one secondary guide circuit 18 may define a closed path.

According to possible embodiments, at least one secondary guide circuit 18 may define an open path.

In accordance with possible embodiments, each of the transport units 14 may comprise a body 26 and a containment member 27 connected to the body 26 and configured to contain a number of absorbent sanitary articles.

According to possible embodiments, the containment member 27 may comprise means for defining the containment compartment of the absorbent sanitary articles so as to be able to group the absorbent sanitary articles in assemblies formed by a desired number of absorbent sanitary articles.

According to possible embodiments, the body 26 may be provided with a first magnetic element 28 configured to magnetically couple to the primary guide circuit 17, and with a second magnetic element 29, opposite to the first magnetic element, configured to magnetically couple to at least one of the secondary guide circuits 18.

In accordance with possible embodiments, the first magnetic element 28 and the second magnetic element 29 can be selectively activated so that the transport unit 14 is coupled to the primary guide circuit 17 or to one of the secondary guide circuits 18 in the coupling tract 13.

According to possible embodiments, the first magnetic element 28 and the second magnetic element 29 may be configured to advance said body 26 along the primary guide circuit 17 and the secondary guide circuit 18.

For example, the primary guide circuit 17 and the secondary guide circuit 18 may be configured in such a way that a variable magnetic field is generated, configured to magnetically couple with the first magnetic element 28 or the second magnetic element 29 in a tract of the primary guide circuit 17 or of the secondary guide circuit 18, so that the body 26 can move along one of these guide circuits 17 and 18.

According to possible embodiments, the movement and/or stopping along the primary guide circuit 17 or the secondary guide circuit 18 may be obtained by means of magnetic movement means, aerostatic movement means, combinations thereof, or other means. For example, the movement may be substantially obtained as in linear magnetic motors.

According to possible embodiments, at least two of the secondary guide circuits 18 have their respective delivery areas 16 facing outwards of the secondary guide circuits 18 along two directions parallel to each other.

According to possible embodiments, at least two of the secondary guide circuits 18 have their respective delivery areas 16 facing outwards of the secondary guide circuits 18 along two directions perpendicular to each other.

According to possible embodiments, at least two secondary guide circuits 18 may have their respective delivery areas 16 facing outwards of the secondary guide circuits 18 along two directions opposite to each other.

In accordance with possible embodiments, the primary guide circuit 17 may have the receiving area 15 facing towards the inside of the primary guide circuit 17 along a first direction D1 at which, during use, the absorbent sanitary articles are supplied, and at least one of the secondary guide circuits 18 may have the delivery area 16 facing outwards of the secondary guide circuit 18 along a second direction D2 opposite to the first direction D1.

According to possible embodiments, the primary guide circuit 17 may have the receiving area 15 where, during use, the absorbent sanitary articles are provided along a first direction D1 facing the inside of the primary guide circuit 17.

In accordance with possible embodiments, at least one of the secondary guide circuits 18 may have the delivery area 16 where, during use, the absorbent sanitary articles are delivered along a direction D2 facing outwards of the secondary guide circuit 18.

According to possible embodiments, the primary guide circuit 17 may comprise a second receiving area 115 functionally connected to the production machine M1 of absorbent sanitary articles.

This allows optimizing the delivery times of the absorbent sanitary articles by the production machine M1, since after having grouped the desired number of absorbent sanitary articles, and while these articles are delivered to the transport unit 14 in the receiving area 15, the production machine M1 groups the absorbent sanitary articles in the second receiving area 115 and then transfers them to the transport unit 14 without interrupting the production cycle.

In accordance with possible embodiments, the present invention also relates to a method for transporting absorbent sanitary articles by means of a transport apparatus 10.

According to possible embodiments, the transport method may comprise a supplying step of the absorbent sanitary articles from the production machine M1 to the transport units 14 in the receiving area 15, wherein each transport unit 14 carries a respective number of absorbent sanitary articles.

In accordance with possible embodiments, the transport method may comprise a setting step of the supply order of the absorbent sanitary articles transported by the transport units 14 for each of the packaging machines C1, C2, C3.

According to possible embodiments, the transport method may comprise a transporting step of absorbent sanitary articles by means of the transport units 14 towards the packaging machines C1, C2, C3.

In accordance with possible embodiments, the transport method may comprise a delivery step of the absorbent sanitary articles to the packaging machines C1, C2, C3 according to the respective set supply order.

According to possible embodiments, the supply step may envisage providing at least two transport units 14 with a different number of absorbent sanitary articles.

According to possible embodiments, the supply step may envisage providing at least two transport units 14 with a different type of absorbent sanitary articles.

According to possible embodiments, the transport apparatus 10 of absorbent sanitary articles may comprise:
- a guide assembly 11 wherein there is at least one receiving area 15 functionally connected to a production machine M of absorbent sanitary articles and at least one delivery area 16 functionally connected to a respective packaging machine C1; and
- a plurality of transport units 14, each one configured to receive the absorbent sanitary articles from the production machine M1 in the receiving area 15 and to transport them to the delivery area 16 along a desired path defined by the guide assembly 11.

According to possible embodiments, the guide assembly 11 may comprise an inlet tract 19 wherein the receiving area 15 is present, an outlet tract 20 wherein the delivery zone 16 is present, an auxiliary inlet tract 21 wherein an auxiliary receiving area 22 is present, and a transit tract 23.

According to possible embodiments, the guide assembly 11 may comprise a first exchange assembly 24 connected to the transit tract 23, to the auxiliary inlet tract 21 and to the outlet tract 20 and defining a first connection path P1 between the transit tract 23 and the outlet tract 20, which includes the auxiliary inlet tract 21, and a second connection path P2 between the transit tract 23 and the outlet tract 20, which does not include the auxiliary inlet tract 21.

In accordance with possible embodiments, the guide assembly 11 may comprise a second exchange assembly 25 connected to the outlet tract 20, the inlet tract 19 and the transit tract 23 and defining a third connection path P3 between the outlet tract 20 and the transit tract 23 which includes the inlet tract 19, and a fourth path P4 between the outlet tract 20 and the transit tract 23, which does not include the inlet tract 19.

In accordance with possible embodiments, the guide assembly 11 may comprise a closed circuit 37 wherein the transit tract 23 and the outlet tract 20 are present.

In accordance with possible embodiments, at least one transport unit 14 may be configured to advance along the closed circuit 37 to proceed from the transit tract 23 to the outlet tract 20 to complete the second connection path P2.

In accordance with possible embodiments, at least one transport unit 14 may be configured to advance along the closed circuit 37 to proceed from the outlet tract 20 to the transit tract 23 to complete the fourth connection path P4.

According to possible embodiments, the first exchange assembly 24 may comprise a first distinct exchange element 38, physically separated and facing the closed circuit 37 and the auxiliary inlet tract 21, in a first coupling tract 113 and in a second coupling tract 213, respectively.

According to possible embodiments, the first exchange assembly 24 comprises a second distinct exchange element 39, physically separated and facing the closed circuit 37 and the auxiliary inlet tract 21, in a third coupling tract 313 and in a fourth coupling tract 413, respectively.

According to possible embodiments, the second exchange assembly 25 may comprise a third distinct exchange element 40, physically separated and facing the closed circuit 37 and the inlet tract 19, in a fifth coupling tract 513 and in a sixth coupling tract 613, respectively.

According to possible embodiments, the second exchange assembly 25 may comprise a fourth distinct exchange element 41, physically separated and facing the closed circuit 37 and the inlet tract 19, in a seventh coupling tract 713 and in an eighth coupling tract 813, respectively.

In accordance with possible embodiments, at least one of the transport units 14 may be configured to pass from the closed circuit 37 to the first exchange element 38 at the first coupling tract 113.

In accordance with possible embodiments, at least one of the transport units 14 may be configured to pass from the first exchange element 38 to the auxiliary inlet tract 21 at the second coupling tract 213.

In accordance with possible embodiments, at least one of the transport units 14 may be configured to pass from the auxiliary inlet tract 21 to the second exchange element 39 at the fourth coupling tract 413.

In accordance with possible embodiments, at least one of the transport units 14 may be configured to pass from the second exchange element 39 to the closed circuit 37 at the third coupling tract 313.

In accordance with possible embodiments, at least one of the transport units 14 may be configured to pass from the closed circuit 37 to the third exchange element 40 at the fifth coupling tract 513.

In accordance with possible embodiments, at least one of the transport units 14 may be configured to pass from the third exchange element 40 to the inlet tract 19 at the sixth coupling tract 613.

In accordance with possible embodiments, at least one of the transport units 14 may be configured to pass from the inlet tract 19 to the fourth exchange element 41 at the eighth coupling tract 813.

In accordance with possible embodiments, at least one of the transport units 14 may be configured to pass from the fourth exchange element 41 to the closed circuit 37 at the seventh coupling tract 713.

According to possible embodiments, at least one transport unit 14 may be configured to pass in succession from the transit tract 23 of the closed circuit 37 to the first exchange element 38 to the auxiliary inlet tract 21 to the second exchange element 39 and to the outlet tract 20 of the closed circuit 37 to complete the first connection path P1.

According to possible embodiments, at least one transport unit 14 may be configured to pass in succession from the outlet tract 20 of the closed circuit 37 to the third exchange element 40 to the inlet tract 19 to the fourth exchange element 41 and to the transit tract 23 of the closed circuit 37 to complete the third connection path P3.

According to possible embodiments, the first exchange assembly 24 may comprise a first distinct open circuit 42, physically separated and facing the closed circuit in a first inlet coupling tract 43 and in a first outlet coupling tract 44 between which the auxiliary inlet tract 21 is comprised.

According to possible embodiments, the first open circuit 42 comprises the auxiliary inlet tract 21.

According to possible embodiments, at least one transport unit 14 may be configured to pass in succession from the transit tract 23 of the closed circuit 37 to the auxiliary inlet tract 21 comprised in the first open circuit 42 and from this to the outlet tract 20 of the closed circuit 37 to complete the first connection path P1.

According to possible embodiments, the second exchange assembly 25 may comprise a second distinct open circuit 45, physically separated and facing the closed circuit 37 in a second inlet coupling tract 46 and in a second outlet coupling tract 47 between which the inlet tract 19 is comprised.

According to possible embodiments, the second open circuit 45 comprises the inlet tract 19.

According to possible embodiments, at least one transport unit 14 may be configured to pass in succession from the outlet tract 20 of the closed circuit 37 to the inlet tract 19 comprised in the second open circuit 45, and from this to the transit tract 23 of the closed circuit 37 to complete the third connection path P3.

According to possible embodiments, at least one of the transport units 14 may be configured to pass from the closed circuit 37 to the first open circuit 42, and vice versa, at the first inlet coupling tract 43 and at the first outlet tract 44, respectively.

According to possible embodiments, at least one of the transport units 14 may be configured to pass from the closed circuit 37 to the second open circuit 45, and vice versa, at the second inlet coupling tract 46 and at the second outlet coupling tract 47, respectively.

According to possible embodiments, at least one transport unit 14 is configured to alternatively follow the first connection path P1 or the second connection path P2.

According to possible embodiments, at least one transport unit 14 is configured to alternatively follow the third connection path P3 or the fourth connection path P4.

Both the configuration illustrated in FIG. 11 and the configuration 12, as well as modifications or combinations of these configurations, allow at least one transport unit 14 to alternatively follow the first connection path P1 or the second connection path P2, and alternatively the third connection path P3 or the fourth connection path P4.

In accordance with possible embodiments, each of the transport units 14 may comprise a body 26 and a containment member 27 connected to the body 26 and configured to contain the absorbent sanitary articles.

According to possible embodiments, the body 26 may be provided with a first magnetic element 28 configured to magnetically couple to a portion of the guide assembly 11 and with a second magnetic element 29, opposite to the first magnetic element 28, configured to magnetically couple to another portion of the guide assembly 11.

In accordance with possible embodiments, the first magnetic element 28 and the second magnetic element 29 may be selectively activated so that the transport unit 14 is coupled to a portion of the guide assembly 11 in one of the coupling tracts 113, 213, 313, 413, 513, 613, 713, 813, 43, 44, 46, and 47.

According to possible embodiments, the containment member 27 may be connected to the body 26 by means of a connecting member 30 configured to rotate around a second rotation axis X2 perpendicular to the direction of movement D defined by the guide circuit 12.

In accordance with possible embodiments, the guide circuit 11 may comprise at least one spiral tract 48 wherein there is a first surface 49 and a second surface 50, opposite to the first surface 49, arranged along a spiral path, so that upon leaving the spiral path the first surface 49 and the second surface 50 are inverted with each other.

According to possible embodiments, the receiving area 15 faces the inside of the guide assembly along a first direction D1, and the delivery area 16 faces the outside of the guide assembly 11 along a second direction D2 parallel to the first direction D1.

According to possible embodiments, at the receiving area 15, during use, the sanitary articles may be supplied towards the inside of the guide assembly 11 along a first direction D1.

According to possible embodiments, at the delivery area 16, during use, the sanitary articles may be supplied towards the outside of the guide assembly 11 along a second direction D2.

According to possible embodiments, at the auxiliary receiving area 22, during use, the sanitary articles may be supplied towards the inside of the guide assembly 11 along a third direction D3.

According to possible embodiments, the third direction D3 may be transversal to the first direction D1.

In accordance with possible embodiments, the guide assembly 11 may comprise a plurality of delivery areas 16 functionally connected to the packaging machine C1.

According to possible embodiments, at least two delivery areas 16 functionally connected to the packaging machine C1 may be oriented towards the outside of the guide assembly 11 along two parallel directions.

According to possible embodiments, the present invention also relates to a movable device 90 for transporting groups G1, G2, G3 of articles in a packaging plant 100.

For illustrative purposes only, and non-limitative to this, below we will refer to absorbent sanitary articles. It is understood that the movable device 90 can also be used to transport groups G1, G2, G3 of articles of other types in a packaging plant 100. For example, the articles may include books, CDs, DVDs, tools, various kinds of objects, bottles, containers, their combinations, or other articles.

In accordance with possible embodiments, the packaging plant 100 may comprise at least one production machine M1, M2, M3 of groups G1, G2, G3 of articles and at least one packaging machine C1, C2, C3 configured to form a desired combination of groups G1, G2, G3 of articles.

According to possible embodiments, the movable device 90 may comprise a frame 51 provided with movement means 52 configured to move the frame 51 in the packaging plant 100 at least from the production machine M1, M2, M3 to the packaging machine C1, C2, C3.

In accordance with possible embodiments, the movement means 52 may comprise wheels, tracks, actuators, motors, transmissions, gears, transmission belts, balls, rollers, and their combinations, or other suitable means for moving the frame 51 in the packaging plant 100.

According to possible embodiments, the movable device 90 may comprise a guide circuit 12 coupled to the frame 51, and at least one transport unit 14.

In accordance with possible embodiments, the transport units may comprise a body 26 and a containment member 27 connected to the body 26 and configured to contain at least one of the groups G1, G2, G3 of articles.

According to possible embodiments, the body 26 may be provided with a first magnetic element 28 configured to magnetically couple to the guide circuit 12, so that, during use, the body 26 is in the desired position along the guide circuit 12.

In accordance with possible embodiments, the body 26 may be configured to position itself in the desired position along the guide circuit 12.

According to possible embodiments, the transport unit 14 may be provided with a second magnetic element 29, opposite to the first magnetic element 28, configured to magnetically couple to another guide circuit 12 distinct and physically separated from said guide circuit 12.

In accordance with possible embodiments, the other guide circuit 12 may be present in the packaging plant 100.

According to possible embodiments, the other guide circuit 12 may be present in another movable device 90.

In accordance with possible embodiments, the first magnetic element 28 and the second magnetic element 29 may be selectively activated so that the transport unit is coupled to the guide circuit 12, or to the other guide circuit 12 at a coupling tract 13 wherein, during use, the guide circuit 12 and the other guide circuit 12 are facing and physically separated from each other.

According to possible embodiments, the movable device 90 may comprise at least two distinct guide circuits 12, physically separated and facing each other in respective coupling tracts 13.

In accordance with possible embodiments, the movable device 90 may comprise a lifting member 53 configured to bring the guide circuit 12 from a first height to a second height different from the first height.

According to possible embodiments, the movable device 90 may comprise a communication unit 54 configured for receiving and transmitting a signal with a control and command unit 36 configured to control the movable device 90 and/or other movable devices 90 present in the packaging plant 100.

In accordance with possible embodiments, the movable device 90 may comprise a rechargeable electric power supply unit 55 configured to power the movable device 90.

For example, the rechargeable electric power supply unit 55 may power the movement means 52 and/or other components of the movable device 90.

According to possible embodiments, the present invention also relates to a packaging plant 100 of groups G1, G2, G3 of articles, comprising at least one production machine M1, M2, M3 of groups G1, G2, G3 of articles and at least one packaging machine C1, C2, C3 configured to form a desired combination of groups G1, G2, G3 of articles.

In accordance with possible embodiments, the packaging plant 100 may comprise a plurality of movable devices 90 as in any of the possible embodiments of the present invention.

According to possible embodiments, the packaging plant 100 may comprise a guide circuit 12 functionally coupled to at least one production machine M1, M2, M3, so that, during use, the transport units 14 can be positioned at the production machine M1, M2, M3.

This aspect allows maintaining the production continuity of the production machine M1, M2, M3 which, after completing the transfer to a movable device 90, does not need to wait for another movable device 90 to deliver the articles to the latter.

This aspect allows the production machine M1, M2, M3 to transfer the produced articles to the transport units 14 present in the guide circuit 12 functionally coupled to the production machine M1, M2, M3.

In this way, the movable devices 90 may position themselves at the guide circuit 12 functionally coupled to the production machine M1, M2, M3 so as to allow the exchange of the transport units 14 with the articles from the guide circuit 12 functionally coupled to the production machine M1, M2, M3 to the guide circuit 12 of the movable device 90 and possibly the simultaneous exchange of the empty or partially empty transport units 14 from the guide circuit 12 of the transport unit 14 to the guide circuit 12 coupled to the production machine M1, M2, M3.

In accordance with possible embodiments, the packaging plant 100 may comprise a guide circuit 12 functionally coupled to at least two packaging machines C1, C2, C3, so that, during use, the transport units 14 can be positioned at any of these packaging machines C1, C2, C3.

According to possible embodiments, the packaging plant 100 may comprise a control and command unit 36 configured to control the plurality of movable devices 90 in a coordinated manner so as to form the desired combination of groups G1, G2, G3 of articles in the packaging machine C1, C2, C3.

In accordance with possible embodiments, the packaging plant 100 may comprise a charging station 56 wherein there is at least one charging device 57 configured to recharge one or more rechargeable electric power supply units 55 of the movable devices 90.

According to possible embodiments, at least one movable device 90 may be provided with transfer means configured to transfer the articles from the transport units 14 to the packaging machines C1, C2, C3.

According to possible embodiments, at least one movable device 90 may be provided with transfer means configured to transfer the articles from the production machines M1, M2, M3 to the transport units 14.

According to possible embodiments, at least one movable device 90 may be provided with transfer means configured to transfer the articles from the transport units 14 of the movable device 90 to the transport units 14 of another movable device 90.

According to possible embodiments, at least one movable device 90 may be provided with transfer means configured to transfer the articles from the transport units 14 of the movable device 90 to the transport units 14 of the guide circuit 12 present in the packaging plant 100.

For example, the transfer means may comprise an articulated robot, an anthropomorphic robot, or other similar means.

It is clear that modifications and/or additions of parts can be made to the embodiments described so far, without thereby departing from the scope of the present invention.

It is also clear that, although the present invention has been described with reference to some specific examples, a person skilled in the art will certainly be able to produce many other equivalent forms having the characteristics set forth in the claims and therefore all falling within the scope of protection defined therein.

In the following claims, the references in brackets have the sole object of facilitating the reading and should not be considered as limiting factors regarding the scope of protection underlying the specific claims.

The invention claimed is:

1. A packaging plant of absorbent sanitary articles for packaging groups of said absorbent sanitary articles, comprising:
   at least one production machine configured for producing said groups of absorbent sanitary articles;
   at least one packaging machine configured for packaging said groups of absorbent sanitary articles, and forming a desired combination of said groups of absorbent sanitary articles;
   a transport apparatus of absorbent sanitary articles functionally connected to said at least one production machine and to said at least one packaging machine and configured for transporting said groups of absorbent sanitary articles from said production machine to said packaging machine in a desired order;
   said transport apparatus of absorbent sanitary articles comprising:
   a guide assembly wherein there is at least one receiving area configured to be functionally connected to a production machine of the at least one production machine of absorbent sanitary articles and at least one delivery area configured to be functionally connected to a respective packaging machine of the at least one packaging machine; and
   a plurality of transport units each configured to receive said absorbent sanitary articles from said production machine in said at least one receiving area and to transport them to said at least one delivery area along a desired path defined by said guide assembly,
   wherein said guide assembly comprises:
   an inlet tract wherein a receiving area of the at least one receiving area is present;
   an outlet tract wherein a delivery area of the at least one delivery area is present;
   an auxiliary inlet tract wherein an auxiliary receiving area is present;
   a transit tract;
   a first exchange assembly connected to said transit tract, to said auxiliary inlet tract and to said outlet tract and defining:
      a first connection path between said transit tract and said outlet tract, which comprises said auxiliary inlet tract, and
      a second connection path between said transit tract and said outlet tract, which does not comprise said auxiliary inlet tract;
   a second exchange assembly connected to said outlet tract, to said inlet tract and to said transit tract, and defining:
      a third connection path between said outlet tract and said transit tract, which comprises said inlet tract, and
      a fourth connection path between said outlet tract and said transit tract, which does not comprise said inlet tract;
   wherein said guide assembly comprises a closed circuit wherein said transit tract and said outlet tract are present;
   wherein said first exchange assembly comprises a first circuit facing said dosed circuit in a first inlet coupling tract and in a first outlet coupling tract between which said auxiliary inlet tract is included;
   wherein said second exchange assembly comprises a second circuit facing said dosed circuit in a second inlet coupling tract and in a second outlet coupling tract between which said inlet tract is included,
   wherein at least one of said transport units is configured to pass from said dosed circuit to said first circuit, and vice versa, respectively, at said first inlet coupling tract and at said first outlet coupling tract;
   wherein at least one of said transport units is configured to pass from said dosed circuit to said second circuit, and vice versa, respectively, at said second inlet coupling tract and at said second outlet coupling tract;
   wherein each of said plurality of transport units comprises a body and a containment member connected to said body and configured to contain said absorbent sanitary articles, wherein said body is provided with a first magnetic element configured to magnetically couple to a portion of said guide assembly,
   wherein said first circuit is an open circuit physically separated from said closed circuit;
   wherein said second circuit is an open circuit physically separated from said closed circuit; and
   wherein said body is provided with a second magnetic element, opposite to said first magnetic element, configured to magnetically couple to another portion of said guide assembly, wherein said first magnetic element and said second magnetic element are selectively activatable so that said transport unit is coupled to a portion of said guide assembly in one of said coupling tracts.

2. The plant as in claim 1, wherein said containment member is connected to said body by means of a connecting member configured to rotate about a rotation axis parallel to a direction of movement defined by a guide circuit.

3. The plant as in claim 2, wherein said connecting member is configured to rotate about a second rotation axis perpendicular to the direction of movement.

4. The plant as in claim 1, wherein at least one of said circuits comprises at least two guide portions placed at different heights and connected to each other by means of a connecting portion, and wherein said transport unit is configured to pass from one guide portion to another guide portion along said connecting portion.

5. The plant as in claim 1, further comprising a control and command unit configured to control said transport units in a coordinated manner to bring said groups of absorbent sanitary articles in the desired order to said packaging machines in relation to the desired combination of said groups of absorbent sanitary articles to be made in each of said packaging machines.

6. The plant as in claim 5, wherein said containment member comprises at least one sensor designed to detect position, weight, and/or number relating to individual absorbent sanitary articles and/or to said groups of absorbent sanitary articles.

7. The plant as in claim 6, wherein said control and command unit is configured to receive signals from each of said transport units (and/or from said at least one sensor, so that it can control the transport units in relation to the signals received, in order to optimize times and paths of each transport unit.

8. The plant as in claim 1, wherein said guide assembly comprises at least one spiral tract wherein there is a first surface and a second surface, opposite to said first surface, arranged along a spiral path, so that at an outlet from said spiral path, said first surface and said second surface are inverted with respect to an inlet of said spiral path.

9. The plant as in claim 1, wherein said receiving area faces towards an inside of said guide assembly along a first direction and said delivery area faces towards an outside of said guide assembly along a second direction parallel to said first direction.

10. The plant as in claim 1, wherein said auxiliary receiving area is configured for carrying out re-pack operations, and wherein an auxiliary transport unit is configured to stop in said auxiliary receiving area and to proceed from said first inlet coupling tract to said first outlet coupling tract at a speed lower than the speed of said auxiliary transport unit in said closed circuit.

11. A managing method of a packaging plant of absorbent sanitary articles for packaging and transporting groups of said absorbent sanitary articles, comprising:
- providing a packaging plant of absorbent sanitary articles according to claim 1;
- a setting step of a supply order of said groups of absorbent sanitary articles for each of said packaging machines;
- a supplying step of said groups of absorbent sanitary articles from one or more production machines to respective transport units;
- a transporting step of said groups of absorbent sanitary articles by means of said transport units towards said packaging machines; and
- a delivery step of said groups of absorbent sanitary articles to said packaging machines according to the respective set supply order.

12. A packaging plant of absorbent sanitary articles for packaging groups of said absorbent sanitary articles, comprising:
- a first number of production machines configured for producing said groups of absorbent sanitary articles, wherein said first number is equal to or greater than one;
- a second number of packaging machines configured for packaging said groups of absorbent sanitary articles; wherein each of said packaging machines is configured to form a desired combination of said croups of absorbent sanitary articles, wherein said second number is equal to or greater than two;
- a transport apparatus functionally connected to said first number of said production machines and to said second number of said packaging machines and configured for transporting said groups of absorbent sanitary articles from said production machines to said packaging machines in a desired order;

wherein said transport apparatus comprises:
- a guide assembly provided with at least two distinct guide circuits, physically separated and facing each other at least in one coupling tract; and
- a plurality of transport units each comprising a body and a containment member connected to a body and configured to contain at least one of said groups of absorbent sanitary articles, said plurality of transport units configured to transport at least one of said groups of absorbent sanitary articles along a desired path defined by said guide circuits, wherein said body is provided with a first magnetic element configured to magnetically couple to one of said guide circuits, and a second magnetic element, opposite to said first magnetic element, configured to magnetically couple to another of said guide circuits, wherein said first magnetic element and said second magnetic element are selectively activatable so that each of said transport units is configured to pass from one of said guide circuits to another of said guide circuits at said coupling tract where said guide circuits are physically separated.

* * * * *

UNITED STATES PATENT AND TRADEMARK OFFICE
CERTIFICATE OF CORRECTION

| | | |
|---|---|---|
| PATENT NO. | : 12,036,102 B2 | Page 1 of 1 |
| APPLICATION NO. | : 17/760509 | |
| DATED | : July 16, 2024 | |
| INVENTOR(S) | : Oronzo Lucia, Massimiliano Rossetti and Francesco D'Aponte | |

It is certified that error appears in the above-identified patent and that said Letters Patent is hereby corrected as shown below:

On the Title Page

Item (71) Applicant address information should be listed as:
- Fameccanica.Data S.p.A., San Giovanni Teatino (Chieti), ITALY -

Signed and Sealed this
Twenty-seventh Day of May, 2025

Coke Morgan Stewart
*Acting Director of the United States Patent and Trademark Office*